(12) United States Patent
Carloni et al.

(10) Patent No.: US 7,723,539 B2
(45) Date of Patent: May 25, 2010

(54) CATALYSTS BASED ON METAL COMPLEXES FOR THE SYNTHESIS OF OPTICALLY ACTIVE CHRYSANTHEMIC ACID

(75) Inventors: Silvia Carloni, Traversetolo (IT); Valerio Borzatta, Bologna (IT); Leni Moroni, Trecasali (IT); Giada Tanzi, Salsomaggiore (IT); Giovanni Sartori, Casalmaggiore (IT); Raimondo Maggi, Parma (IT)

(73) Assignee: ENDURA S.p.A., Bologna (IT)

( * ) Notice: Subject to any disclaimer, the term of this patent is extended or adjusted under 35 U.S.C. 154(b) by 0 days.

(21) Appl. No.: 11/629,182

(22) PCT Filed: Jun. 14, 2005

(86) PCT No.: PCT/EP2005/052740

§ 371 (c)(1),
(2), (4) Date: Dec. 8, 2006

(87) PCT Pub. No.: WO2005/123254

PCT Pub. Date: Dec. 29, 2005

(65) Prior Publication Data

US 2008/0021237 A1 Jan. 24, 2008

(30) Foreign Application Priority Data

Jun. 16, 2004 (IT) .............................. MI04A1211

(51) Int. Cl.
*C07C 61/04* (2006.01)
(52) U.S. Cl. ........................................ 562/506; 502/150
(58) Field of Classification Search ....................... None
See application file for complete search history.

(56) References Cited

U.S. PATENT DOCUMENTS

| | | | | |
|---|---|---|---|---|
| 4,996,349 A * | 2/1991 | Krief et al. | .................... | 560/124 |
| 5,004,840 A * | 4/1991 | Krief et al. | .................... | 568/486 |
| 5,296,595 A * | 3/1994 | Doyle | .......................... | 540/200 |
| 5,298,623 A * | 3/1994 | Masamune et al. | .......... | 548/101 |
| 5,767,276 A * | 6/1998 | Zhang | ............................ | 546/2 |
| 6,072,081 A * | 6/2000 | Itagaki et al. | ............... | 562/506 |
| 6,242,377 B1 * | 6/2001 | Hirahata et al. | ............. | 502/117 |
| 6,268,525 B1 * | 7/2001 | Itagaki et al. | ............... | 562/401 |
| 6,307,057 B1 * | 10/2001 | MacMillan et al. | ...... | 548/316.4 |
| 6,316,620 B1 * | 11/2001 | Busacca | ..................... | 544/243 |
| 6,410,741 B1 * | 6/2002 | Itagaki et al. | ............... | 548/237 |
| 6,534,434 B2 * | 3/2003 | MacMillan et al. | ......... | 502/167 |
| 6,670,500 B2 * | 12/2003 | Kamitamari et al. | ........ | 560/124 |
| 6,858,559 B2 * | 2/2005 | Yamamoto et al. | .......... | 502/165 |
| RE38,947 E * | 1/2006 | Doyle | .......................... | 540/200 |
| 7,288,674 B2 * | 10/2007 | Itagaki et al. | ............... | 562/506 |
| 2002/0013475 A1 * | 1/2002 | MacMillan et al. | ...... | 548/311.1 |
| 2002/0123645 A1 * | 9/2002 | Suzukamo et al. | .......... | 562/401 |
| 2002/0177718 A1 * | 11/2002 | Yamamoto et al. | .......... | 548/101 |
| 2003/0233003 A1 * | 12/2003 | Itagaki et al. | ................. | 556/32 |
| 2007/0185343 A1 * | 8/2007 | Verpoort et al. | ............... | 556/30 |

FOREIGN PATENT DOCUMENTS

| | | | |
|---|---|---|---|
| EP | 0933349 A1 | | 4/1999 |
| FR | 2826298 A1 | * | 12/2002 |
| HU | 210648 B | * | 6/1995 |
| JP | 49014448 A | * | 2/1974 |
| JP | 49102650 A | * | 9/1974 |
| JP | 52017448 A | * | 2/1977 |
| JP | 09208521 A | * | 8/1997 |

OTHER PUBLICATIONS

Suenobu, et al. JAOCS 2004 126(23) 7271-7280.*
Zang et al. Chinese Chem Letters (1991), 2 (2), 169-70.*
Lisheng Cai et al., Binuclear Versus Mononuclear Copper Complexes as Catalysts for Asymmetric Cyclopropanation of Styrene, Tetrahedron: *Asymmetry* 10 (1991) 411-427.
Lowenthal et al., Asymmetric Copper-Catalyzed Cyclopropanation of Trisubstituted and Unsymmetrical CIS-1,2-Disubstituted Olefins: Modified Bis-Oxazoline Ligands, Tetrahedron Letter, vol. 32, No. 50. pp. 7373-7376 (1991).
Burgete et al., Bis (Oxazoline) Copper Complexes Covalently Bonded to Insoluble Support as Catalysts in Cyclopropanation Reactions, *J. Org. Chem.* 66, 8893-8901 (2001).
Burguete et al., Polymer-Supported Bis (Oxazoline)—Copper Complexes as Catalysts in Cyclopropanation Reactions, Organic Letters, vol. 2, No. 24, 3905-3908 (2000).
Minutolo et al., Heterogeneous Asymmetric Epoxidation of Unfunctionalized Olefins Catalyzed by Polymer-Bound (Salen) Manganese Complexes, *Tetrahedron: Asymmetry*. vol. 7, No. 8, pp. 2293-2302 (1996).

* cited by examiner

*Primary Examiner*—Daniel M Sullivan
*Assistant Examiner*—Chukwuma O Nwaonicha
(74) *Attorney, Agent, or Firm*—Abelman, Frayne & Schwab

(57) ABSTRACT

Catalysts are described based on metal complexes derived from optically active s compounds, chosen from the classes consisting of bisoxazolines and salicylaldimines supported on an organic or inorganic matrix and employed in particular for the synthesis of optically active chrysanthemic acid.

6 Claims, No Drawings

CATALYSTS BASED ON METAL COMPLEXES FOR THE SYNTHESIS OF OPTICALLY ACTIVE CHRYSANTHEMIC ACID

FIELD OF THE INVENTION

The present invention relates to:

catalysts based on metal complexes with ligands derived from optically active compounds chosen from the classes consisting of bisoxazolines and salicylaldimines supported on an organic or inorganic matrix and employed in particular for the synthesis of esters of optically active chrysanthemic acid;

the process for preparing said catalysts, the process for preparing esters of optically active chrysanthemic acid using said catalysts.

STATE OF THE ART

Derivatives of optically active chrysanthemic acid are important insecticide intermediates.

(+)-Trans-2,2-dimethyl-3-(2-methyl-1-propenyl)cyclopropanecarboxylic acid, for example, is a component of synthetic pyrethroids. The insecticidal activity of the corresponding esters (pyrethroids) in the trans form is usually higher than that of the corresponding cis isomer. In particular the esters (pyrethroids) of (+)-trans chrysanthemic acid or the esters (pyrethroids) of chrysanthemic acid enriched in the (+)-trans form show excellent insecticidal activity.

Many methods are known for producing an optically active chrysanthemic acid by a synthetic process. Particularly known are methods in which a racemic chrysanthemic acid in the correct diastereoisomeric trans/cis ratio is reacted with a suitable resolving agent, such as optically active amines, to obtain an enantiomerically enriched chrysanthemic acid.

For example in FR 1,536,458 a separation method is described for racemic trans/cis chrysanthemic acid using a suitable optically active resolving amine to obtain (+)-trans chrysanthemic acid; in GB 1,364,730 and U.S. Pat. No. 3,879,451 a separation method is also described for racemic trans/cis chrysanthemic acid with suitable optically active resolving amines to obtain a mixture of (+)-trans/(+)-cis chrysanthemic acid.

In Tetrahedron Lett., 1991, 32, 7373 a method is described for obtaining enantiomerically enriched chrysanthemic acid by reacting a prochiral olefin with a diazoacetic ester in the presence of an asymmetric copper complex, using optically active ligands such as bisoxazolines.

In EP 933349 A1 a method is described for obtaining enantiomerically enriched chrysanthemic acid by reacting a prochiral olefin with a diazoacetic ester in the presence of an asymmetric copper complex, using optically active ligands such as salicylaldimines.

However all these methods present drawbacks isolation of enantiomerically enriched chrysanthemic acid by means of optically active resolving amines involves the use of various solvents for crystallising the corresponding diastereoisomeric salts and subsequent recovery of the resolving amine, resulting in a costly process with many passages. The synthesis of enantiomerically enriched chrysanthemic acid by chiral catalysts is expensive since the catalysts can be used only once and therefore this method is not industrially advantageous.

SUMMARY OF THE INVENTION

The applicant has surprisingly found that catalysts with chiral ligands able to complex with transition metal ions and anchor themselves by suitable "spacer" chains to organic or inorganic type matrices can be used for many reaction cycles in the preparation of esters of enantiomerically enriched chrysanthemic acid by reacting a prochiral olefin with a suitable diazoacetic ester.

The present invention therefore provides supported complexes of formula (A)

(A)

in which Supp is an organic or inorganic type matrix, Met is a transition metal ion chosen from groups VIII and Ib, L is a ligand containing at least one asymmetric carbon atom and at least one spacer chain which forms covalent bonds with said organic or inorganic type matrix, said ligand being coordinated by complexation to the aforesaid transition metal ions. The ligand L is derived from a ligand $L_a$ chosen from the classes consisting of (1) optically active bisoxazolines and (2) optically active salicylaldimines.

DETAILED DESCRIPTION OF THE INVENTION

Met is preferably a metal ion chosen from the class consisting of Cu, Co, Ru, Pt, Rh, Ir, even more preferably being $Cu^{++}$.

When Supp is an inorganic type matrix, it is preferably a silica matrix; when Supp is an organic type matrix, it is preferably a polymer matrix, even more preferably chosen from the class consisting of styrene polymers, styrene/divinylbenzene copolymers, hydropolysiloxanes.

When $L_a$ is chosen from the optically active bisoxazoline class (1), $L_a$ preferably has the general formula (B)

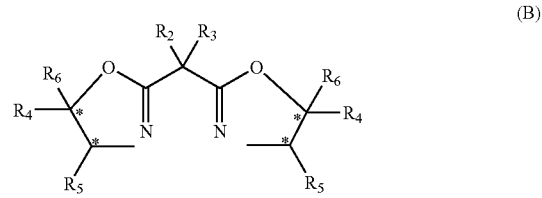

(B)

where * indicates a stereogenic centre, where $R_2$ and $R_3$, the same or different, are hydrogen, $C_1$-$C_{12}$ linear or branched alkyl, $C_3$-$C_{11}$ alkenyl, $C_7$-$C_{11}$ aralkyl unsubstituted or substituted with groups able to polymerise or by groups able to bind to an organic or inorganic polymer matrix, with the proviso that at least one of the $R_2$ and $R_3$ groups has a functionality able to polymerise or able to bind to an organic or inorganic polymer matrix;

$R_4$, $R_5$ and $R_6$, the same or different, are hydrogen, $C_4$-$C_8$ linear or branched alkyl, phenyl unsubstituted or substituted with one, two, three $C_1$-$C_4$ alkyl groups, $C_7$-$C_{11}$ aralkyl, naphthyl or $R_4$ and $R_5$, bound together, are a 1,2-indandiyl group.

Particularly preferred meanings for $R_2$ and $R_3$, the same or different, are $C_1$-$C_4$ linear or branched alkyl, $C_3$-$C_{11}$ alkenyl, $C_1$-$C_2$ trialkoxy silyl propyl, benzyl, vinylbenzyl, benzyl substituted by a 3-thio-1-hexyl $C_1$-$C_2$ trialkoxy silyl.

Particularly preferred meanings for $R_4$, R5 and $R_6$, the same or different, are hydrogen, $C_1$-$C_4$ alkyl, phenyl, naphthyl, $C_7$-$C_{11}$ aralkyl, 1,2-indandiyl.

Even more preferably when $L_a$ is a ligand of formula (B)

$R_2$ and $R_3$, the same or different, are chosen from methyl, allyl, 6-hepten-1-yl, 10-undecen-1-yl, vinylbenzyl, 4-(3-thio-1-hexyl-6-trimethoxy silyl)benzyl;

$R_4$, $R_5$, $R_6$, the same or different, are chosen from hydrogen, phenyl, naphthyl, benzyl, 1,2-indandiyl.

Even more preferred compounds of class (1) are those in which $L_a$ is chosen from the compounds of formula (B) in which:

$R_2$=$R_3$=4-vinylbenzyl, $R_4$=H, $R_5$ bound to $R_6$=1,2-indandiyl.

$R_2$=$R_3$=4-vinylbenzyl, $R_4$=H, $R_5$=$R_6$=phenyl, $R_2$=$R_3$=allyl, $R_4$=H, $R_5$ bound to $R_6$=1,2-indandiyl $R_2$=$R_3$=allyl, $R_4$=H, $R_5$=$R_6$=phenyl, $R_2$=$R_3$=6-hepten-1-yl $R_4$=H, $R_5$=$R_6$=phenyl, $R_2$=$R_3$=10-undecen-1-yl, $R_4$=H, $R_5$=$R_6$=phenyl.

When $L_a$ is chosen from the optically active salicylaldimine class (2), it preferably has the general formula (C)

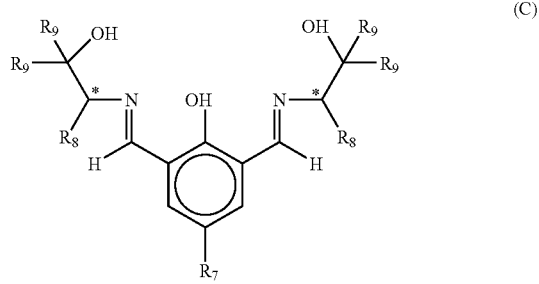

(C)

in which * indicates a stereogenic centre where $R_7$ is hydrogen, $C_1$-$C_{12}$ alkyl, $C_2$-$C_{11}$ alkenyl, phenyl unsubstituted or substituted by $C_1$-$C_4$ alkyl groups or $C_2$-$C_{11}$ alkenyl groups, or is a —$OR_{10}$ group, where $R_{10}$ is $C_1$-$C_8$ alkyl, $C_3$-$C_{11}$ alkenyl, phenyl unsubstituted or substituted by a $C_2$-$C_{11}$ alkenyl group, benzyl unsubstituted or substituted by a $C_2$-$C_{11}$ alkenyl group;

$R_8$ is $C_1$-$C_4$ alkyl, phenyl, benzyl;

$R_9$ is a group of formula (D)

(D)

where $R_{11}$ is hydrogen, $C_1$-$C_8$ alkyl; $R_{12}$ is $C_1$-$C_8$ alkyl, $C_3$-$C_{11}$ alkenyl, benzyl unsubstituted or substituted with a vinyl group.

When $R_7$ or $R_9$ possess alkenyl functionality, the compounds of formula (C) are able to polymerise forming a polymer matrix or are able to bind to an already formed organic or inorganic polymer matrix.

Particularly preferred meanings for $R_7$ are hydrogen, linear or branched $C_1$-$C_4$ alkyl, $C_2$-$C_{11}$ alkenyl, phenyl unsubstituted or substituted with $C_2$-$C_3$ alkenyl groups, or a —$OR_{10}$ group, where $R_{10}$ is $C_3$-$C_{11}$ alkenyl, phenyl substituted with a $C_2$-$C_3$ alkenyl group, benzyl substituted with a $C_2$-$C_3$ alkenyl group.

Particularly preferred meanings for $R_8$ are $C_1$-$C_4$ linear or branched alkyl, benzyl. A particularly preferred meaning for $R_9$ is a group of formula (D) where $R_{11}$ is $C_1$-$C_8$ linear or branched alkyl and $R_{12}$ is $C_4$-$C_8$ linear or branched alkyl, $C_3$-$C_{11}$ alkenyl, benzyl unsubstituted or substituted with a vinyl group.

Even more preferably $R_7$ is chosen from methyl, tert-butyl, phenyl, vinyl phenyl, or a —$OR_{10}$ group in which $R_{10}$ is allyl, 6-hepten-1-yl, 10-undecen-1-yl, vinylphenyl, vinylbenzyl; $R_8$ is chosen from methyl, benzyl; $R_9$ is a group of formula (D) where $R_{11}$ is tert-butyl, tert-octyl; $R_{12}$ is n-butyl, n-octyl, allyl, 6-hepten-1-yl, 10-undecen-1-yl, benzyl, vinylbenzyl.

Even more preferred compounds of class (2) are those in which $L_a$ is chosen from one of the compounds of formula (C) in which:

$R_7$=$R_8$=methyl, $R_9$ is a group of formula (D) in which $R_{11}$=tert-butyl, $R_{12}$=allyl.

$R_7$=$R_8$=methyl, $R_9$ is a group of formula (D) in which $R_{11}$=tert-butyl, $R_{12}$=6-hepten-1-yl, $R_7$=$R_8$=methyl, $R_9$ is a group of formula (D) in which $R_{11}$=tert-butyl, $R_{12}$=10-undecen-1-yl $R_7$=$R_8$=methyl, $R_9$ is a group of formula (D) in which $R_{11}$=tert-butyl, $R_{12}$=benzylvinyl, $R_7$=—$OR_{10}$, $R_{10}$=4-vinylbenzyl, $R_8$=methyl, $R_9$ is a group of formula (D) in which $R_{11}$=tert-butyl, $R_{12}$=octyl $R_7$=vinylphenyl, $R_8$=methyl, $R_9$ is a group of formula (D) in which $R_{11}$=tert-butyl, $R_{12}$=octyl, $R_7$=—$OR_{10}$, $R_{10}$=allyl, $R_8$=methyl, $R_9$ is a group of formula (D) in which $R_{11}$=tert-butyl, $R_{12}$=octyl, $R_7$=—$OR_{10}$, $R_{10}$=10-undecen-1-yl, $R_8$=methyl, $R_9$ is a group of formula (D) in which $R_{11}$=tert-butyl, $R_{12}$=octyl.

A further aspect of the present invention is the process for preparing catalysts of formula (A) which comprises the following steps:

a) heterogenization of the ligand $L_a$ to obtain the intermediate adduct (A')

Supp-L      (A')

in which L has the same meanings as $L_a$ with the only difference that the spatial chain has formed covalent bonds with the organic or inorganic matrix;

b) treatment of the adduct (A') obtained in the preceding step with a solution of a transition metal salt to obtain the complex of formula (A).

In the process of the present invention step a) can be conducted by one of the following alternative methods as described for example in Tetrahedron: Asymm., 1996, 7, 2293 and J. Org. Chem., 2001, 66, 8893:

a1) Copolymerisation with suitable monomers such as styrene/divinylbenzene;

a2) Copolymerisation with hydropolysiloxanes;

a3) Tethering onto an inorganic silica matrix.

Copolymerisation with styrene/divinylbenzene [method a1)] is conducted on the products of formula (B) where $R_2$ and/or $R_3$ are preferably 4-vinylbenzyl or on the products of formula (C) in which $R_7$ and/or $R_9$ preferably contain the benzylvinyl residue with a radical promoter preferably chosen from azobisisobutyronitrile (AIBN) or a peroxide, such as tert-butyl peroxide or lauroyl peroxide, in a suitable aromatic solvent such as toluene, at the reflux temperature of the solvent itself. In this manner copolymers are obtained in which the quantity of L is determined by elemental analysis.

Copolymerisation with hydropolysiloxanes [method a2)] is conducted on the products of formula (B) where $R_2$ and/or $R_3$ are $C_3$-$C_{11}$ alkenyl, preferably allyl, 6-heptene-1-yl and 10-undecen-1-yl and on the compounds of formula (C) in which $R_7$ and/or $R_9$ contain $C_3$-$C_{11}$ alkenyl functionality preferably allyl, 6-hepten-1-yl and 10-undecen-1-yl, in the presence of a hydrosilylation catalyst such as divinyltetramethyldisiloxane platinum (0) in a suitable organic solvent, such as toluene, at room temperature. In this manner copolymers are obtained in which the quantity of L is determined by elemental analysis.

Tethering on the inorganic silica matrix [method a3)] is conducted by reacting the products of formula (B) where $R_2$ and/or $R_3$ are groups of formula:

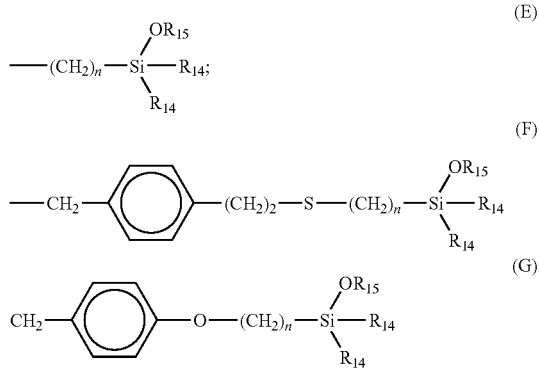

where n is an integer between 3 and 11, $R_{14}$ is $C_1$-$C_2$ alkyl or a —$OR_{15}$ group where $R_{15}$ is $C_1$-$C_2$ alkyl, n=3 is preferred.

Tethering can be conducted with compounds of formula (C) in which $R_7$ is a group containing a residue of formula (E), (F), (G) in which (E), (F), (G) are as previously defined, on commercial silica matrices having surface areas of from 50 to 600 m$^2$/g for example SP18-9638.03 (Grace GmbH & Co, Germany) and ICN Silica 63-200 (ICN Biomedicals GmbH, Germany), in toluene under reflux, removing the alcohol which forms during the reaction.

In step b) when the catalyst of formula (A) is to be obtained in which Met is $Cu^{++}$ the salt used is preferably an organic copper salt; in accordance with a particularly preferred embodiment the salt used is chosen from cupric trifluoromethanesulfonate or cupric acetate monohydrate. In accordance with a particularly preferred embodiment the cupric trifluoromethanesulfonate is used when Supp-L is obtained by heterogenization of the bisoxazolines of formula (B). In this case in accordance with a particularly preferred embodiment Supp-L is treated with an equimolar solution of cupric trifluoromethanesulfonate in a suitable non-polar organic solvent, being preferably dichloromethane.

In accordance with another preferred embodiment the cupric acetate monohydrate is instead used when $Cu^{++}$ is to be complexed with the suitable Supp-L obtained by heterogenization of salicylaldimines of formula (C). In this case in accordance with a further particularly preferred embodiment, Supp-L is treated with a cupric acetate monohydrate solution in methanol in a molar amount being double that of L, and in the presence of stirring an organic base such as triethylamine, pyridine, methylpyridine at room temperature and under stirring. The mixture is then filtered and the solid product is washed with dichloromethane and dried at 25° C./0.133 mbar.

The heterogeneous catalyst of formula (A) is used in the process for preparing optically active chrysanthemic acid or enriched in one of its enantiomers, which in particular comprises:

1) cyclopropanation reaction of a diacetate of formula (H) with 2,5-dimethyl-2,4-hexadiene

where $R_1$ is a linear or branched $C_1$-$C_8$ alkyl, possibly substituted by one or two $C_5$-$C_{10}$ alicyclic groups, $C_6$-$C_{10}$ aryl unsubstituted or substituted by 1, 2, 3, $C_1$-$C_4$ alkyl groups, $C_7$-$C_{11}$ aralkyl unsubstituted or substituted on the ring with 1, 2, 3 $C_1$-$C_4$ alkyl groups, a $C_5$-$C_{10}$ alicyclic group unsubstituted or substituted with 1, 2, 3 $C_1$-$C_4$ alkyl groups or cyclohexyl;

2) acid or alkaline hydrolysis of the ester group.

Preferred meanings of $R_1$ are $C_1$-$C_4$ linear or branched alkyl, phenyl, benzyl, dimethylbenzyl, cyclohexyl, cycloheptyl, cyclooctyl, dicyclohexylmethyl (d,l)-menthyl.

The chrysanthemic acid obtained with this process has a trans isomer percentage not lower than 50% and an enantiomeric excess (e.e.), expressed as chrysanthemic acid (+)-trans, of between 20 and 90%.

The compounds of formula (B) can be obtained as described for example in Helv. Chim. Acta, 1991, 74, 1, by reacting a malonimidate dihydrochloride of formula (M)

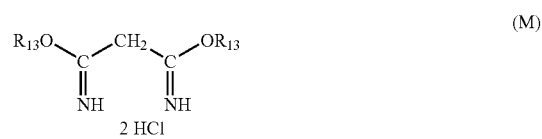

where $R_{13}$ is methyl, ethyl
with an alcohol of formula (N)

where * indicates a stereogenic centre where $R_4$, $R_5$, $R_6$ have the previously indicated meanings, in a suitable solvent such as a chlorinated solvent or a dipolar aprotic solvent in the presence of an organic base chosen for example from aliphatic tertiary amines or pyridine, at a temperature between 20° C. and the solvent reflux temperature to give a product of formula (O).

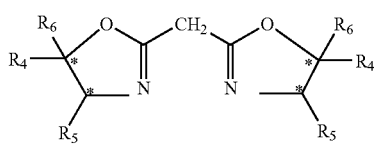 (O)

where * indicates a stereogenic centre where $R_4$, $R_5$ and $R_6$ have the aforesaid meanings.

The product of formula (O) is then reacted with a product of formula (P) and/or (Q) in the suitable stoichiometric ratio $R_2Hal$ (P)

$R_3Hal$ (Q)

where $R_2$ and $R_3$ have the aforesaid meanings and Hal is chlorine, bromine, iodine, chlorine being preferred, in a suitable dipolar aprotic solvent at a temperature not higher than 40° C. in the presence of an inorganic or organic metal base such as sodium amide, sodium hydride, lithium diisopropylamide, butyllithium, to give the compound of formula (B).

Suitable dipolar aprotic solvents are for example N,N-dimethylformamide, dimethylsulfoxide, acetonitrile, N,N-dimethylacetamide, N-methylpyrrolidone, N-butyl pyrrolidone, N-cyclohexyl pyrrolidone, tetramethylenesulfone.

The compounds of formula (C) can be obtained as described for example in Tetrahedron: Assym., 1999, 10, 411 by reacting the suitable dialdehyde of formula (R)

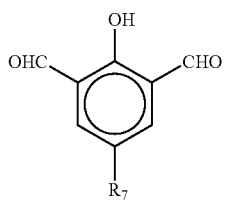 (R)

where $R_7$ has the aforesaid meaning, with an equivalent quantity of an amino alcohol of formula (S)

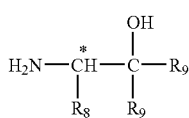 (S)

where * indicates a stereogenic centre where $R_8$ and $R_9$ have the aforesaid meanings, in a water soluble alcoholic solvent, such as methanol, ethanol, propanol, isopropanol at room temperature. The products of formula (R) where $R_7$ has the meaning $—OR_{10}$ are obtained by the following passages starting from hydroquinone:

i) Monoesterification reaction with $R_{10}Hal$ where $R_{10}$ has the aforesaid meanings and Hal is chlorine, bromine, iodine in a dipolar aprotic solvent such as N,N-dimethylformamide, N,N-dimethylacetamide, N-methyl pyrrolidone, dimethylsulfoxide, tetramethylenesulfone in the presence of an inorganic base such as sodium hydroxide, sodium carbonate, potassium carbonate.

ii) Dimethylolation reaction with aqueous formaldehyde in suitable stoichiometric ratios, in the presence of an inorganic base and a suitable water soluble solvent, at room temperature to obtain the corresponding benzyl dialcohol.

iii) Oxidation reaction of the derived benzyl dialcohol with suitable oxidising agents such as manganese dioxide.

When the products of formula (R) contain $R_7$ which is different from $—OR_{10}$, they are obtained from the corresponding phenols of formula (T),

 (T)

where $R_7$ has the aforesaid meanings, by the dimethylolation and oxidation reactions as aforedescribed.

The products of formula (S), where $R_8$ and $R_9$ have the aforesaid meanings, are obtained by reacting a suitable amino ester hydrochloride of formula (U)

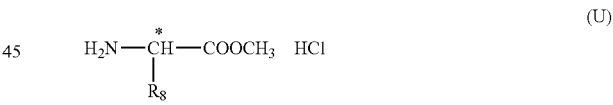 (U)

where * indicates a stereogenic centre and where R8 has the aforesaid meanings with a product of formula (V)

$R_9MgHal$ (V)

where R9 has the aforesaid meanings and Hal is chlorine, bromine, iodine, in an ether solvent, such as ethyl ether, isopropyl ether, tetrahydrofuran, methyl tetrahydrofuran at room temperature and in a stoichiometric ratio (V):(U)=4:1 as given for example in Tetrahedron: Assym., 1999, 10, 411.

Non-limiting examples for illustrative purposes are given hereinafter for preparing the supported metal complexes of formula (A) of the present invention and of the process for preparing chrysanthemic acid using said catalysts.

EXAMPLE 1

Synthesis of 2,2'-methylenebis[3α,8α-dihydro-(3aR, 3'aR,8aS,8'aS)]-8H-indene[1,2-d]oxazole Ligand of Formula B, with $R_2=R_3=R_4=H$, $R_5$ Bound to $R_6=1,2$-indandiyl

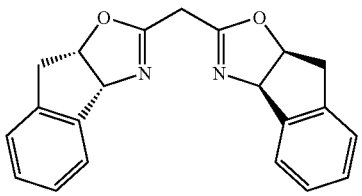

A mixture of 1.155 g (5.0 mmol) diethyl malonimidate hydrochloride, 20 ml of 1,1,1-trichloroethane, 1.492 g (10.0 mmol) of (1R,2S)-(+)-cis-1-amino-2-indanole and 1.40 ml (10.0 mmol) of triethylamine are heated under reflux for 16 hours. The mixture is cooled to 25° C. and evaporated under reduced pressure (40° C./24 mbar). The solid product obtained is recrystallised from a 1:1 (v/v) mixture of methanol:dichloromethane, to provide 0.933 g of product whose $^1$H-NMR and mass spectra are consistent with the structure shown.

$[\alpha]_D=+350°$ (c=1, $CH_2Cl_2$).

EXAMPLE 2

Synthesis of 2,2'-methylenebis[4,5-dihydro-(4R,5S)-diphenyl]oxazole Ligand of Formula (B), with $R_2=R_3=R_4=H$, $R_5=R_6=$phenyl

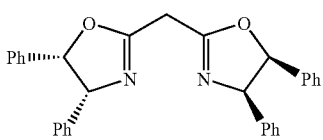

A mixture of 2.133 g (10.0 mmol) of (1S,2R)-(+)-2-amino-1,2-diphenylethanol and 1.155 g (5 mmol) of diethyl malonimidate hydrochloride in 20 ml of 1,2-dichloroethane are heated under reflux for one hour. A solution composed of 1.40 ml (10 mmol) of triethylamine and 5 ml of 1,2-dichloroethane are added drop-wise over 30 minutes and the mixture is maintained under reflux for a further 3.5 hours. The mixture is cooled to 25° C., the solid that forms is filtered off and the solution is evaporated under reduced pressure (40° C./24 mbar). The solid product obtained is recrystallised from a 1:1 (v:v) mixture of methanol:dichloromethane, to produce 1.589 g of product whose $^1$H-NMR and mass spectra are consistent with the structure shown.

$[\alpha]_D=+159.5°$ (c=0.5,$CHCl_3$).

EXAMPLE 3

Synthesis of [3aR,3'aR,8aS,8'aS]-2,2'-[2-(4-vinylphenyl)-1-(4-vinylbenzyl)ethylidene]bis[3α,8α-dihydro-8H-indeno[1,2-d]oxazole Ligand of Formula (B), with $R_2=R_3=$4-vinylbenzyl, $R_4=H$, $R_5$ Bound to $R_6=1,2$-indandiyl

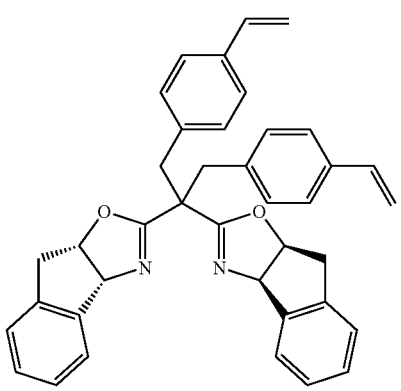

0.264 g (0.8 mmol) of the compound whose preparation is described in example 1 are added to a mixture of 0.076 g (1.9 mmol) NaH (60% in oil) in 10 ml of DMSO and 5 ml of 1,4-dioxane. The mixture is stirred at 25° C. for one hour, then a solution of 0.24 ml (1.7 mmol) of 4-vinylbenzylchloride in 3 ml DMSO is added. The mixture is left under stirring for a further 3 hours at 40° C., cooled to 25° C. then diluted with 10 ml of dichloromethane. The mixture is stirred with a 1M HCl solution (2×20 ml). The organic phase is separated, dried over $Na_2SO_4$, filtered and evaporated under reduced pressure (50° C./24 mbar). After purifying through a silica gel column (eluent=hexane:ethyl acetate 1:1 (v/v)) 0.427 g of solid product are obtained whose $^1$H-NMR and mass spectra are consistent with the expected structure.

$[\alpha]_D=+206.9°$ (c=0,62,$CH_2Cl_2$)

EXAMPLE 4

Synthesis of 2,2'-[2-(4-vinylphenyl)-1-(4-vinylbenzyl)ethylidene]bis[4,5-dihydro-(4R,5S)-diphenyl]oxazole Ligand of Formula (B), with $R_2=R_3=$4-vinylbenzyl, $R_4=H$, $R_6=R_6=$phenyl

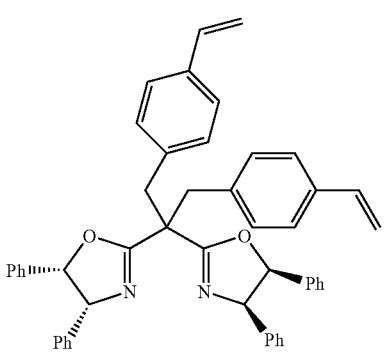

A mixture of 0.1 g (2.5 mmol) of NaH (60% in oil) in 30 ml of DMSO and 5 ml of 1,4-dioxane are added to 0.55 g (1.2 mmol) of the compound whose preparation is described in example 2. The mixture is stirred at 25° C. for 5 minutes until a homogeneous solution is obtained, then 0.40 ml (2.6 mmol) of 4-vinylbenzylchloride are added. The mixture is left under stirring for a further 3 hours at 40° C., then cooled to 25° C., diluted with 20 ml of dichloromethane then extracted with a 1 M HCl solution (3×30 ml). The organic phase is separated, dried over $Na_2SO_4$, filtered and evaporated under reduced pressure (50° C./24 mbar). After purifying through a silica gel column (eluent=hexane:ethyl acetate 7:3 (v/v)) and subsequent recrystallisation from a methane:dichloromethane 1:1 (v:v) solution, 0.706 g of solid product are obtained whose $^1$H-NMR and mass spectra are consistent with the expected structure.

$[\alpha]_D = +347.21°$ (c=1.004, $CH_2Cl_2$).

EXAMPLE 5

Synthesis of 2,2'-(1-allylbutyl-3-enylidene)bis[4,5-dihydro-(4R,5S)-diphenyl]oxazole Ligand of Formula (B), with $R_2=R_3=$allyl, $R_4=$H, $R_5=R_6=$phenyl

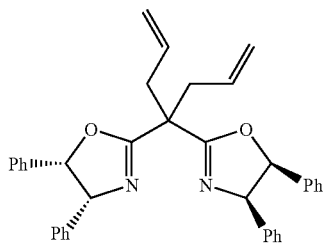

0.275 g (0.6 mmol) of the compound whose preparation is described in example 2 are added to a mixture of 0.05 g (1.25 mmol) 60% NaH in oil in 15 ml of DMSO and 2.5 ml of 1,4-dioxane. The mixture is stirred for 5 minutes at 25° C. then 0.11 ml (1.3 mmol) of allyl bromide are added. The mixture is again stirred for a further 3 hours at 40° C. The solution is cooled to room temperature and diluted with 10 ml $CH_2Cl_2$. An aqueous 1M HCl solution (3×15 ml) is added to the mixture. The organic phase is separated, dried over $Na_2SO_4$, filtered and evaporated under reduced pressure (20° C./24 mbar) to obtain a product which, after purifying through a silica gel column (eluent=hexane:ethyl acetate 6:4 (v/v)) and subsequent recrystallisation from a methanol:dichloromethane 1:1 (v/v) solution, 0.264 g of solid product are obtained whose $^1$H-NMR and mass spectra are consistent with the expected structure.

$[\alpha]_D = +365.07°$ (c=1.002, $CH_2Cl_2$).

EXAMPLE 6

Synthesis of 2,2'-[1-(10-undecen-1-yl)dodec-11-enylidene]bis[4,5-dihydro-(4R,5S)-diphenyl]oxazole Ligand of Formula (B), $R_2=R_3=$10-undecen-1-yl, $R_4=$H, $R_5=R_6=$phenyl

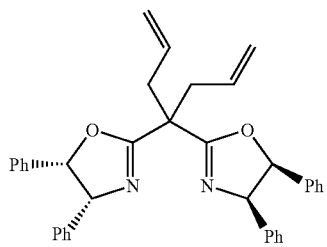

0.275 g (0.6 mmol) of the compound whose preparation is described in example 2 are added to a mixture of 0.05 g (1.25 mmol) 60% NaH in oil in 15 ml of DMSO and 2.5 ml of 1,4-dioxane. The mixture is stirred for 5 minutes at 25° C. and then 0.28 ml (1.3 mmol) of 11-bromo-1-undecene are added. The mixture is again stirred for a further 3 hours at 40° C. The solution is cooled to room temperature and diluted with 10 ml of $CH_2Cl_2$. An aqueous 1M HCl solution (3×15 ml) is added to the mixture. The organic phase is separated, dried over $Na_2SO_4$, filtered and evaporated under reduced pressure (20° C./24 mbar) to obtain a product which after purifying through a silica gel column (eluent=hexane:ethyl acetate 8:2 (v/v)) appears as a solid (0.332 g) whose $^1$H-NMR and mass spectra are consistent with the expected structure.

$[\alpha]_D = +123.3°$ (c=0.504, $CH_2Cl_2$).

EXAMPLE 7

Heterogenization of the Compound of Example 3 on Silica Matrix (ICN 63-200)

A mixture containing 30 ml of chloroform, 0.337 g (0.6 mmol) of the compound whose preparation is described in example 3, 0.238 ml (1.2 mmol) of 95% 3-mercaptopropyltrimethoxysilane and 0.164 g (1.0 mmol) of AIBN are refluxed under mechanical stirring for 15 hours. The solution is evaporated under reduced pressure (30° C./24 mbar), to obtain an oily product to which are added 25 ml of toluene and 2 g of commercial silica ICN Silica 63-200 (ICN Biomedicals GmbH, Germany) previously dried in a muffle furnace at 400° C. for 5 hours. The suspension is heated under reflux temperature under magnetic stirring for 24 hours, then cooled to 25° C. and filtered. The solid thus obtained is washed with dichloromethane and maintained under reflux with a 1:1 (v/v) dichloromethane:diethyl ether mixture for 16 hours in a Soxhlet extractor. The product thus obtained is dried under reduced pressure (25° C./0.013 mbar) for 3 hours.

From the elemental analysis, the degree of loading of the supported ligand is calculated to be equal to 0.21 mmol/g (N=0.58%).

0.114 g (0.315 mmol) of $Cu(OTf)_2$ in 45 ml of dichloromethane are added to 1.50 g (0.315 mmol) of the above product. The product thus complexed with the Cu(II) is filtered off and dried at 20° C./0.014 mbar.

The copper content is determined by EA-ICP-MS analysis (atomic emission-inductively-coupled-plasma-mass spectometry).

EXAMPLE 8

Heterogenization of the Compound of Example 4 on Silica Matrix (ICN 63-200)

A mixture containing 26 ml of chloroform, 0.41 g (0.6 mmol) of the compound whose preparation is described in example 4, 0.238 ml (1.2 mmol) of 95% 3-mercaptopropyltrimethoxysilane and 0.174 g (1.06 mmol) of AIBN are refluxed under mechanical stirring for 15 hours. The solution is evaporated under reduced pressure (20° C./24 mbar), to obtain an oily product to which are added 26 ml of toluene and 2 g of commercial silica ICN Silica 63-200 (ICN Biomedicals GmbH, Germany) previously dried in a muffle furnace at 400° C. for 5 hours. The suspension is heated under reflux under magnetic agitation for 24 hours, then cooled to 25° C. and filtered. The solid thus obtained is washed with dichloromethane and maintained under reflux with a 1:1 (v/v) dichloromethane:diethyl ether mixture for 16 hours in a Soxhlet extractor. The product thus obtained is dried under reduced pressure (20° C./0.013 mbar) for 3 hours.

From the elemental analysis, the degree of loading of the supported ligand is calculated to be equal to 0.19 mmol/g (N=0.53%).

0.0814 g (0.225 mmol) of $Cu(OTf)_2$ in 45 ml of dichloromethane are added to 1.18 g (0.225 mmol) of the product thus obtained. The product thus complexed with the Cu(II) is filtered off and dried at 20° C./0.014 mbar.

The copper content is determined by EA-ICP-MS analysis.

EXAMPLE 9

Heterogenization of the Compound of Example 4 on Silica Matrix (SP18-9758.01)

A mixture containing 26 ml of chloroform, 0.41 g (0.6 mmol) of the compound whose preparation is described in example 4, 0.238 ml (1.2 mmol) of 95% 3-mercaptopropyltrimethoxysilane and 0.174 g (1.06 mmol) of AIBN is refluxed under mechanical stirring for 15 hours. The solution is evaporated under reduced pressure (20° C./24 mbar), to obtain an oily product to which are added 26 ml of toluene and 2 g of commercial silica SP18-9758.01 (Grace GmbH & Co, Germany) previously dried in a muffle furnace at 400° C. for 5 hours. The suspension is heated to reflux under magnetic stirring for 24 hours, then cooled to 25° C. and filtered. The solid thus obtained is washed with dichloromethane and maintained under reflux with a 1:1 (v/v) dichloromethane:diethyl ether mixture for 16 hours in a Soxhlet extractor. The product thus obtained is dried by using a vacuum mechanical pump (20° C./0.013 mbar) for 3 hours.

From the elemental analysis, the degree of loading of the supported ligand is calculated to be equal to 0.165 mmol/g (N=0.47%).

0.0814 g (0.225 mmol) of $Cu(OTf)_2$ in 45 ml of dichloromethane are added to 1.36 g (0.225 mmol) of the above product. The product thus complexed with the Cu(II) is filtered off and dried at 20° C./0.014 mbar.

The copper content is determined by EA-ICP-MS analysis.

EXAMPLE 10

Heterogenization of the Compound of Example 5 on Silica Matrix (SP18-9758.01)

In the manner described in example 7, 0.263 g (0.49 mmol) of the compound whose preparation is described in example 5, 0.185 ml (0.98 mmol) of 95% 3-mercaptopropyltrimethoxysilane are reacted with 0.121 g (0.738 mmol) of AIBN in 20 ml of toluene. After adding 1.6 g of commercial silica SP18-9758.01 (Grace GmbH & Co, Germany) previously dried in a muffle furnace at 400° C. for 5 hours, a solid is obtained by using the previously described method.

The degree of loading of the supported ligand is equal to 0.15 mmol/g (N=0.43%).

0.054 g (0.15 mmol) of $Cu(OTf)_2$ in 50 ml of dichloromethane are added to 1.06 g (0.16 mmol) of the product thus obtained. The product thus complexed with the Cu(II) is filtered off and dried at 20° C./0.014 mbar.

The copper content is determined by EA-ICP-MS analysis.

EXAMPLE 11

Heterogenization of the Compound of Example 6 on Silica Matrix (SP18-9758.01)

In the manner described in example 7, 0.227 g (0.35 mmol) of the compound whose preparation is described in example 6, 0.132 ml (0.7 mmol) of 95% 3-mercaptopropyltrimethoxysilane are reacted with 0.086 g (0.525 mmol) of AIBN in 18 ml of toluene. After adding 1.2 g of commercial silica SP18-9758.01 (Grace GmbH & Co, Germany) previously dried in a muffle furnace at 400° C. for 5 hours, a solid is obtained by using the previously described method.

The degree of loading of the supported ligand is equal to 0.135 mmol/g (N=0.39%).

0.054 g (0.15 mmol) of $Cu(OTf)_2$ in 50 ml of dichloromethane are added to 1.18 g (0.16 mmol) of the above product. The product thus complexed with the Cu(II) is filtered off and dried at 20° C./0.014 mbar.

The copper content is determined by EA-ICP-MS analysis.

EXAMPLE 12

Heterogenization of the Compound of Example 4 on Polystyrene Matrix 0.037 g (0.054 mmol) of the compound whose preparation is described in example 4, 0.27 ml of styrene (2.38 mmol) and 0.26 ml of 80% technical divinylbenzene (meta:para=2:1) are dissolved in 5 ml of toluene. 0.008 g of AIBN are added and the mixture is heated under reflux for 20 hours under vigorous stirring. 10 ml of methanol are added and a precipitate is obtained which is filtered off. The solid obtained is washed with $CH_2Cl_2$ and MeOH (2×50 ml) then ground to obtain a powder.

The degree of loading of supported ligand is equal to 0.125 mmol/g (N–0.35%). 0.054 g (0.15 mmol) of $Cu(OTf)_2$ in 50 ml of dichloromethane are added to 1.2 g (0.16 mmol) of the above product. The product thus complexed with the Cu(II) is filtered off and dried at 20° C./0.014 mbar.

The copper content is determined by EA-ICP-MS analysis.

EXAMPLE 13

Synthesis of Chrysanthemic Acid Promoted by the Heterogeneous Catalyst Described in Example 9

1.44 g of heterogeneous catalyst complexed with the copper, whose preparation is described in example 9, are suspended in 45 ml of dichloromethane and 64 ml (450 mmol) of 2,5-dimethyl-2,4-hexadiene. A solution of 10.08 g (45 mmol) of l-menthyl diazoacetate in 67.5 ml of dichloromethane is added at 25° C. over 2 hours. At the end of the addition stirring is prolonged for a further 3 hours. The catalyst is removed by filtration and washed with 50 ml of dichloromethane. Excess 2,5-dimethyl-2,4-hexadiene is recovered quantitatively from the reaction crude product by distillation at 138° C. 6.9 g of chrysanthemic acid l-menthyl ester are obtained.

After removing the solvent under reduced pressure (20° C./24 mbar), the crude reaction product is hydrolysed in a hydroalcoholic alkaline environment.

After acidification and extraction with dichloromethane, chrysanthemic acid is obtained with the following composition:
cis/trans=20/80; $ee_{cis}$=35%; $ee_{trans}$=71%.

EXAMPLE 14

Synthesis of Chrysanthemic Acid Promoted by the Recycled Heterogeneous Catalyst of Example 13

In the manner described in example 13, the catalyst, recovered after the first reaction cycle and dried for 1 hour at 20° C./0.014 mbar, is reused in two further catalytic cycles to obtain 5.4 g of l-menthyl chrysanthemate in both cycles.

After hydrolysis of the ester, the chrysanthemic acid has the following composition.
$2^{nd}$ cycle: cis/trans=20/80; $ee_{cis}$=35%; $ee_{trans}$=70%
$3^{rd}$ cycle: cis/trans=21/79; $ee_{cis}$=35%; $ee_{trans}$=66%.

EXAMPLE 15

Synthesis of Chrysanthemic Acid Promoted by the Heterogeneous Catalyst Described in Example 10

0.11 g of the heterogeneous catalyst whose preparation is described in example 10 are suspended in 3 ml of dichloromethane and 4.2 ml (30 mmol) of 2,5-dimethyl-2,4-hexadiene. In the manner described in example 13, the mixture is reacted with a solution of 0.672 g (3 mmol) l-menthyl diazoacetate in 4.5 ml dichloromethane. 0.74 g of l-menthyl chrysanthemate are obtained. Following basic hydrolysis, acidification and extraction with dichloromethane, chrysanthemic acid is obtained with the following composition.
cis/trans=16/84; $ee_{cis}$=15%; $ee_{trans}$=72%

EXAMPLE 16

Synthesis of Chrysanthemic Acid Promoted by the Recycled Catalyst of Example 15

In the manner described in example 13, the catalyst, recovered after the first reactive cycle described in example 15 and dried for 1 hour at 20° C./0.014 mbar, is reused to obtain 0.48 g of l-menthyl chrysanthemate.

Following hydrolysis of the ester, the chrysanthemic acid has the following composition:
$2^{nd}$ cycle: cis/trans=20/80; $ee_{cis}$=7%; $ee_{trans}$=47%.

EXAMPLE 17

Synthesis of Chrysanthemic Acid Promoted by the Heterogeneous Catalyst Described in Example 11

0.12 g of heterogeneous catalyst whose preparation is described in example 11, are suspended in 3 ml of dichloromethane and 4.2 ml (30 mmol) of 2,5-dimethyl-2,4-hexadiene. In the manner described in example 13, the mixture is reacted with a solution of 0.672 g (3 mmol) of l-menthyl diazoacetate in 4.5 ml dichloromethane. 0.74 g of l-menthyl chrysanthemate are obtained.

Following basic hydrolysis, acidification and extraction with dichloromethane, chrysanthemic acid is obtained with the following composition.
cis/trans=18/82; $ee_{cis}$=23%; $ee_{trans}$=68%

EXAMPLE 18

Synthesis of Chrysanthemic Acid Promoted by the Recycled Catalyst of Example 17

In the manner described in example 13, the catalyst, recovered after the first reactive cycle described in example 17 and dried for 1 hour at 20° C./0.014 mbar, is reused to obtain 0.54 g of l-menthyl chrysanthemate.

Following hydrolysis of the ester, the chrysanthemic acid has the following composition.
$2^{nd}$ cycle: cis/trans=19/81; $ee_{cis}$=23%; $ee_{trans}$=67%

EXAMPLE 19

Synthesis of Chrysanthemic Acid Promoted by the Heterogeneous Catalyst Described in Example 8

0.182 g of heterogeneous catalyst whose preparation is described in example 8 are suspended in 3 ml of dichloromethane and 4.2 ml (30 mmol) of 2,5-dimethyl-2,4-hexadiene. A solution of 0.613 g (3 mmol) of 2-phenyl-2-propyl diazoacetate in 4.5 ml of dichloromethane is then added at 25° C. over 2 hours and the mixture is stirred for a further 3 hours. The catalyst is filtered and washed with 10 ml of dichloromethane. The excess 2,5-dimethyl-2,4-hexadiene is recovered quantitatively from the reaction crude product (138° C./1 bar). 0.30 g of 2-phenyl-2-propyl chrysanthemate are obtained. After basic hydrolysis, acidification and extraction with dichloromethane, chrysanthemic acid with the following composition is obtained:
cis/trans=27/73; $ee_{cis}$=65%; $ee_{trans}$=70%

EXAMPLE 20

Synthesis of Chrysanthemic Acid Promoted by the Heterogeneous Catalyst Described in Example 8

0.182 g of heterogeneous catalyst whose preparation is described in example 8 are suspended in 3 ml of dichloromethane and 4.2 ml (30 mmol) of 2,5-dimethyl-2,4-hexadiene. A solution of 0.793 g (3 mmol) of dicyclohexylmethyl diazoacetate in 4.5 ml of dichloromethane is then added at 25° C. over 2 hours and the mixture is stirred for a further 3 hours. Following the same method described in example 13, 0.47 g of dicyclohexylmethyl chrysanthemate are obtained. After basic hydrolysis, acidification and extraction with dichloromethane chrysanthemic acid with the following composition is obtained:
cis/trans=17/83; $ee_{cis}$=42%; $ee_{trans}$=70%

EXAMPLE 21

Synthesis of Chrysanthemic Acid Promoted by the Heterogeneous Catalyst Described in Example 7

0.148 g of heterogeneous catalyst whose preparation is described in example 7 are suspended in 3 ml of dichloromethane and 4.2 ml (30 mmol) of 2,5-dimethyl-2,4-hexadiene. A solution of 0.672 g (3 mmol) of l-menthyl diazoacetate in 4.5 ml of dichloromethane is then added at 25° C. over 2 hours and the mixture is stirred for a further 3 hours. Following the same method described in example 13. 0.31 g of l-menthyl chrysanthemate are obtained. After basic hydrolysis, acidification and extraction with dichloromethane chrysanthemic acid with the following composition is obtained:

cis/trans=26/74; $ee_{cis}$=4%; $ee_{trans}$=26%

EXAMPLE 22

Synthesis of Chrysanthemic Acid Promoted by the Heterogeneous Catalyst Described in Example 12

0.13 g of heterogeneous catalyst whose preparation is described in example 12 are suspended in 3 ml of dichloromethane and 4.2 ml (30 mmol) of 2,5-dimethyl-2,4-hexadiene. A solution of 0.672 g (3 mmol) of l-menthyl diazoacetate in 4.5 ml of dichloromethane is then added at 25° C. over 2 hours and the mixture is agitated for a further 3 hours. Following the same method described in example 13, 0.34 g of l-menthyl chrysanthemate are obtained. After basic hydrolysis, acidification and extraction with dichloromethane chrysanthemic acid with the following composition is obtained:

cis/trans=19/81; $ee_{cis}$=23%; $ee_{trans}$=63%

EXAMPLE 23

Synthesis of Chrysanthemic Acid Promoted by the Recycled Heterogeneous Catalyst of Example 22

The catalyst recovered after the first reactive cycle in example 22 and dried for 1 hour at 20° C./0.014 mbar, is reused in two other catalytic cycles using the method described in example 22, to obtain 0.37 g of l-menthyl chrysanthemate in the second cycle and 0.31 g of l-menthyl chrysanthemate in the third cycle.

The chrysanthemic acid has the following composition:
$2^{nd}$ cycle: cis/trans=17/83; $ee_{cis}$=34%; $ee_{trans}$=74%
$3^{rd}$ cycle: cis/trans=18/82; $ee_{cis}$=35%; $ee_{trans}$=74%

EXAMPLE 24

Synthesis of Chrysanthemic Acid Promoted by the Heterogeneous Catalyst Described in Example 9

1.1 g of heterogeneous catalyst [(loading=0.175 mmol/g and already complexed with 0.068 g (0.19 mmol) of Cu(OTf)$_2$] prepared following the procedure described in example 9, are diluted with 2.2 g of the same silica (commercial silica SP18-9758,01, Grace GmbH & Co, Germany) used for anchoring and inserted in a reaction column. A solution containing 4 ml of ethyl diazoacetate (38 mmol), 54 ml of 2,5-dimethyl-2,4-hexadiene (380 mmol) and 75 ml of dichloromethane is loaded into a dropping funnel placed over the column containing the silica material and passed trough the heterogeneous catalyst at room temperature over about 6 hours by nitrogen flow. At the end the catalyst is washed with dichloromethane and dried under nitrogen.

2.83 g of ethyl chrysanthemate are obtained. Following basic hydrolysis, acidification and dichloromethane extraction chrysanthemic acid with the following composition is obtained:

cis/trans=37/63; $ee_{cis}$=43%; $ee_{trans}$=59%.

EXAMPLE 25

Synthesis of Chrysanthemic Acid Promoted by the Recycled Heterogeneous Catalyst of Example 24

The catalyst used in the first cycle of the reaction of example 24 is reused in a further five catalytic cycles by using the same method and the same reagents described in example 24. Ethyl crysanthemate is obtained in the following quantities:
$2^{nd}$ cycle: 2.97 g
$3^{rd}$ cycle: 2.83 g
$4^{th}$ cycle: 2.92 g
$5^{th}$ cycle: 2.75 g
$6^{th}$ cycle: 2.53 g Following basic hydrolysis, acidification and extraction with dichloromethane chrysanthemic acid with the following composition is obtained:
$2^{nd}$ cycle: cis/trans=36/64; $ee_{cis}$=40%; $ee_{trans}$=59%.
$3^{rd}$ cycle: cis/trans=36/64; $ee_{cis}$=42%; $ee_{trans}$=59%
$4^{th}$ cycle: cis/trans=36/64; $ee_{cis}$=40%; $ee_{trans}$=56%
$5^{th}$ cycle: cis/trans=36/64; $ee_{cis}$=40%; $ee_{trans}$=56%
$6^{th}$ cycle: cis/trans=36/64; $ee_{cis}$=40%; $ee_{trans}$=56%

EXAMPLE 26

Synthesis of 2-hydroxy-5-[(-vinylbenzyl)oxy]isophthalaldehyde

A. 4-[(4-Vinylbenzyl)oxy]phenol: 2.8 ml (20 mmol) of 4-vinylbenzylchloride and 2.8 g (20 mol) of potassium carbonate are added to a mixture of 2.2 g (20 mmol) of hydroquinone and 40 ml of acetone. The mixture is heated under reflux for 48 hours under stirring then cooled to room temperature and the solid obtained is filtered off. The solution is evaporated under reduced pressure at 30° C./24 mbar. The residue is purified by means of chromatography through a silica gel column (eluent: dichloromethane) to obtain 1 g (4.4 mmol) of the product, whose $^1$H NMR and mass spectra are consistent with the expected structure.

B. 2,6-Bis(hydroxymethyl)-4-[(4-vinylbenzyl)oxy]phenol: 2.5 ml of 2.6 M NaOH and 1 ml of 37% aqueous formaldehyde (10.5 mmol) are added to 1 g (4.4 mmol) of the previously obtained product dissolved in 2 ml of THF. The mixture is left under stirring at room temperature for 48 hours. After adding 10 ml of a 0.1 M HCl solution the mixture is extracted with ethyl acetate (2×15 ml). The organic phases are pooled and evaporated at 30° C./24 mbar. The crude reaction product is purified by chromatography through a silica gel column (eluent=hexane:ethyl acetate 1:1(v/v)). 0.82 g (2.86 mmol) of product are obtained whose $^1$H NMR and mass spectra are consistent with the expected structure.

C. 2-hydroxy-5-[(4-vinylbenzyl)oxy]isophthalaldehyde: 0.82 g (2.86 mmol) of the aforedescribed product are dissolved in 50 ml of chloroform and to it are then added 1.75 g (20 mmol) of MnO$_2$. The mixture is heated under reflux for about 20 hours, then cooled to room temperature, filtered and washed with dichloromethane (100 ml) and methanol (100 ml). The wash solvents are pooled with the organic solution, then evaporated under reduced pressure (30° C./24 mbar). The residue is purified by means of chromatography through a silica gel column (eluent: hexane:ethyl acetate 1:1 (v:v)) to obtain 0.12 g (0.42 mmol) of the desired dialdehyde, whose $^1$H NMR and mass spectra are consistent with the expected structure.

EXAMPLE 27

Synthesis of 5-(allyloxy)-2-hydroxy isophthalaldehyde

A. 4-(Allyloxy)phenol: 2.6 ml (30 mmol) of allylbromine and 4.1 g (30 mmol) of potassium carbonate are added to a mixture of 3.3 g (30 mmol) of hydroquinone and 40 ml of acetone. The mixture is heated under reflux for 48 hours under stirring, cooled to room temperature and the solid obtained is filtered off. The solution is evaporated under reduced pressure at 30° C./24 mbar. The residue is purified by means of chromatography through a silica gel column (eluent: dichloromethane) to obtain 1.6 g (10.6 mmol) of product whose $^1$H NMR and mass spectra are consistent with the expected structure.

B. 4-allyloxy-2,6-bis(hydroxymethyl)phenol: 6 ml of 2.8 M NaOH and 2.2 ml of 37% aqueous formaldehyde (27 mmol) are added to 1.6 g (10.6 mmol) of 4-(allyloxy)phenol dissolved in 5 ml of THF. The mixture is left under stirring at room temperature for 48 hours. After adding 15 ml of a 0.1 M HCl solution the mixture is extracted with ethyl acetate (2×20 ml). The organic phases are pooled and evaporated under reduced pressure at 30° C./24 mbar. The reaction crude product is purified by chromatography through a silica gel column (eluent=hexane:ethyl acetate 6:4 (v:v)). 1.09 g (5.2 mmol) of product are obtained whose $^1$H NMR and mass spectra are consistent with the expected structure.

C. 5-(allyloxy)-2-hydroxy isophthalaldehyde: 1.09 g (5.2 mmol) of the aforesaid product are dissolved in 30 ml of chloroform then 4.5 g (50 mmol) of $MnO_2$ are added. The mixture is heated under reflux for about 20 hours then cooled to room temperature, filtered and washed with dichloromethane (100 ml) and methanol (100 ml). The wash solvents are pooled with the organic solution, then evaporated under reduced pressure (30° C./24 mbar). The residue is purified by means of chromatography through a silica gel column (eluent=hexane:ethyl acetate 1:1 (v/v)) to obtain 0.063 g (0.3 mmol) of the desired dialdehyde whose $^1$H NMR and mass spectra are consistent with the expected structure.

EXAMPLE 28

Synthesis of 2-hydroxy-5-(10-undecenyloxy)isophthalaldehyde

A. 4-(10-Undecenyloxy)phenol: 9 ml (40 mmol) of 11-bromo-1-undecene and 5.5 g (40 mmol) of potassium carbonate are added to a mixture of 4.4 g (40 mmol) hydroquinone and 40 ml of acetone. The mixture is heated under reflux for 48 hours under stirring, then cooled to room temperature and the solid obtained is filtered off. The solution is evaporated under reduced pressure at 30° C./24 mbar. The residue is purified by means of chromatography through a silica gel column (eluent=hexane:ethyl acetate 4:1 (v/v)) to obtain 2.5 g (9.5 mmol) of product, whose $^1$H NMR and mass spectra are consistent with the expected structure.

B. 2,6-Bis(hydroxymethyl)-4-(10-undecenyloxy)phenol: 5.8 ml of 2.4 M NaOH and 2 ml of 37% aqueous formaldehyde (25 mmol) are added to 2.4 g (9.4 mmol) of 4-(10-undecenyloxy)phenol dissolved in 5 ml of THF. The mixture is left under stirring at room temperature for 48 hours. After adding 15 ml of a 0.1 M HCl solution the mixture is extracted with ethyl acetate (2×20 ml). The organic phases are pooled and evaporated under reduced pressure at 30° C./24 mbar. The crude reaction product is purified by chromatography through a silica gel column (eluent=hexane:ethyl acetate 1:1 (v:v)). 0.39 g (1.2 mmol) of product are obtained whose $^1$H NMR and mass spectra are consistent with the expected structure.

C. 2-Hydroxy-5-(10-undecenyloxy)isophthalaldehyde: 0.39 g (1.2 mmol) of the aforedescribed product are dissolved in 15 ml of chloroform and 1.3 g (15 mmol) of $MnO_2$ are then added. The mixture is heated under reflux for about 20 hours, then cooled to room temperature, filtered and washed with dichloromethane (80 ml) and methanol (80 ml). The wash solvents are pooled with the organic solution, and evaporated under reduced pressure (30° C./24 mbar). The residue is purified by means of chromatography through a silica gel column (eluent=hexane:ethyl acetate 1:1 v:v)) to obtain 0.04 g (0.125 mmol) of the desired dialdehyde. $^1$H NMR and mass spectra are consistent with the expected structure.

EXAMPLE 29

Synthesis of 4-hydroxy-4'-vinyl[1,1'-biphenyl]-3,5-dicarbaldehyde

A. 3,5-bis(hydroxymethyl)-4'-vinyl[1,1'-biphenyl]-4-ol: 8 ml of 6.8 M NaOH and 7.3 ml of 37% aqueous formaldehyde (90 mmol) are added to 7 g (36 mmol) of 4'-vinyl[1,1'-biphenyl]-4-ol dissolved in 8 ml of THF. The mixture is left under stirring at room temperature for 48 hours. After adding 25 ml of a 0.1 M HCl solution the mixture is extracted with ethyl acetate (2×20 ml). The organic phases are pooled and evaporated under reduced pressure at 30° C./24 mbar. The crude reaction product is purified by chromatography through a silica gel column (eluent=hexane:ethyl acetate 1:1 (v:v)). 3.2 g (12.5 mmol) of product are obtained whose $^1$H NMR and mass spectra are consistent with the expected structure.

B. 4-Hydroxy-4'-vinyl[1,1'-biphenyl]-3,5-dicarbaldehyde: 3.2 g (12.5 mmol) of the aforesaid product are dissolved in 30 ml of chloroform and 10.5 g (120 mmol) of $MnO_2$ are added. The mixture is heated under reflux for about 20 hours, then cooled to room temperature, filtered and washed with dichloromethane (120 ml) and methanol (120 ml). The wash solvents are pooled with the organic solution, then evaporated under reduced pressure (30° C./24 mbar). The residue is purified by means of chromatography through a silica gel column (eluent=hexane:ethyl acetate 1:1 v:v)) to obtain 0.22 g (0.86 mmol) of the desired dialdehyde, whose $^1$H NMR and mass spectra are consistent with the expected structure.

EXAMPLE 30

Synthesis of (R)-(−)-2-amino-1,1-di-(5'-tert-butyl-2'-octyloxy-phenyl)-1-propanol 0.03 g of $I_2$ are added to 0.56 g (23.6 mmol) of Mg shavings and 8 g (23.6 mmol) of 2-bromo-4-tert-butyl-1-octyloxybenzene in 5 ml of THF. The mixture is heated to reflux until the metallic Mg is spent, then returned to room temperature. 15 ml of THF and 0.83 g (5.9 mmol) of D-alanine methyl ester hydrochloride are added. The mixture is stirred at room temperature for 16 hours; 20 ml of ethyl ether and 25 ml of a saturated aqueous $NH_4Cl$ solution are added. The organic phase is separated, and the aqueous phase is washed with ethyl ether (3×15 ml). The organic phases are pooled and dried over $Na_2SO_4$. The mixture is filtered and evaporated under reduced pressure (25° C./24 mbar). The crude product is purified by means of chromatography through a silica gel column (eluent=$CH_2Cl_2$:MeOH 25:1 (v:v)). 2.1 g (3.5 mmol) of product are obtained whose $^1$H NMR and mass spectra are consistent with the expected structure $[\alpha]_D$=+34.6° (c=1.034, $CH_2Cl_2$)..

EXAMPLE 31

Synthesis of (R)-(−)-2-amino-1,1-di-(2'-allyloxy-5'-tert-butyl-phenyl)-1-propanol 0.015 g of $I_2$ are added to 0.34 g (14 mmol) of Mg shavings and 3.8 g (14 mmol) of 1-allyloxy-2-bromo-4-tert-butyl-benzene in 3 ml of THF. The mixture is heated to reflux until the metallic Mg is spent, then returned to room temperature. 10 ml of THF and 0.42 g (3 mmol) of D-alanine methyl ester hydrochloride are added. The mixture is stirred at room temperature for 16 hours; 10 ml of ethyl ether and 15 ml of a saturated aqueous $NH_4Cl$ solution are added. The organic phase is separated and the aqueous phase is washed with ethyl ether (3×10 ml). The organic phases are pooled and dried over $Na_2SO_4$. The mixture is filtered and evaporated under reduced pressure (25° C./24 mbar). The crude product is purified by means of chromatography through a silica gel column (eluent=hexane:ethyl acetate 1:1 (v:v)). 0.48 g (1.06 mmol) of product are obtained whose $^1H$ NMR and mass spectra are consistent with the expected structure.

$[\alpha]_D = +41.2°$ (c=1.09, $CH_2Cl_2$)

EXAMPLE 32

Synthesis of (R)-(−)-2-amino-1,1-di-(5'-tert-butyl-2'-hept-6-enyloxy-phenyl)-1-propanol 0.015 g of $I_2$ are added to 0.3 g (12.3 mmol) of Mg shavings and 4 g (12.3 mmol) of 2-bromo-4-tert-butyl-1-hept-6-enyloxy-benzene in 3 ml of THF. The mixture is heated to reflux until the metallic Mg is spent, then returned to room temperature. 15 ml of THF and 0.49 g (3.5 mmol) of D-alanine methyl ester hydrochloride are added. The mixture is stirred at room temperature for 16 hours; 10 ml of ethyl ether and 15 ml of a saturated aqueous $NH_4Cl$ solution are added. The organic phase is separated and the aqueous phase is washed with ethyl ether (3×10 ml). The organic phases are pooled and dried over $Na_2SO_4$. The mixture is filtered and evaporated under reduced pressure (25° C./24 mbar). The crude product is purified by means of chromatography through a silica gel column (eluent=from hexane:ethyl acetate 4:1 (v:v) to hexane:ethyl acetate 1:9 (v:v)). 0.95 g (1.69 mmol) of product are obtained whose $^1H$ NMR and mass spectra are consistent with the expected structure.

$[\alpha]_D = +30.5°$ (c=1.28, $CH_2Cl_2$)

EXAMPLE 33

Synthesis of (R)-(−)-2-amino-1,1-di-(5'-tert-butyl-2'-und-10-ecenyloxy-phenyl)-1-propanol 0.02 g of $I_2$ are added to 0.44 g (18 mmol) of Mg shavings and 6.86 g (18 mmol) of 2-bromo-4-tert-butyl-1-und-10-ecenyloxy-benzene in 8 ml of THF. The mixture is heated to reflux until the metallic Mg is spent, then returned to room temperature. 15 ml of THF and 0.63 g (4.5 mmol) of D-alanine methyl ester hydrochloride are added. The mixture is stirred at room temperature for 16 hours; 25 ml of ethyl ether and 20 ml of a saturated aqueous $NH_4Cl$ solution are added. The organic phase is separated and the aqueous phase is washed with ethyl ether (3×20 ml). The organic phases are pooled and dried over $Na_2SO_4$. The mixture is filtered and evaporated under reduced pressure (25° C./24 mbar). The crude product is purified by means of chromatography through a silica gel column (eluent=from hexane:ethyl acetate 4:1 (v:v) to hexane:ethyl acetate 1:9 (v:v)). 1.8 g (2.66 mmol) of product are obtained whose $^1H$ NMR and mass spectra are consistent with the expected structure.

$[\alpha]_D = +21.7°$ (c=1.06, $CH_2Cl_2$)

EXAMPLE 34

Synthesis of (R)-(−)-2-amino-1,1-di-[5'-tert-butyl-2'(4-vinyl-benzyloxy)-phenyl)]-1-propanol 0.035 g of $I_2$ are added to 0.49 g (20 mmol) of Mg shavings and 6.9 g (20 mmol) of 2-bromo-4-tert-butyl-1-(4-vinyl-benzyloxy)-benzene in 8 ml of THF. The mixture is heated to reflux until the metallic Mg is spent, then returned to room temperature. 20 ml of THF and 0.56 g (4 mmol) of D-alanine methyl ester hydrochloride are added. The mixture is stirred at room temperature for 16 hours; 25 ml of ethyl ether and 20 ml of a saturated aqueous $NH_4Cl$ solution are added. The organic phase is separated and the aqueous phase is washed with ethyl ether (3×15 ml). The organic phases are pooled and dried over $Na_2SO_4$. The mixture is filtered and evaporated under reduced pressure (25° C./24 mbar). The crude product is purified by means of chromatography through a silica gel column (eluent=$CH_2Cl_2$:MeOH 25:1 (v:v)). 1.18 g (1.95 mmol) of product are obtained whose $^1H$ NMR and mass spectra are consistent with the expected structure.

$[\alpha]_D = +19.9°$ (c=0.60, $CH_2Cl_2$)

EXAMPLE 35

Synthesis of (R)-(−)-2-amino-1,1-di-(5'-tert-butyl-2'-octyloxy-phenyl)-3-phenyl-1-propanol 0.02 g of $I_2$ are added to 0.33 g (13.5 mmol) of Mg shavings and 4.63 g (13.5 mmol) of 2-bromo-4-tert-butyl-1-octyloxy-benzene in 5 ml of THF. The mixture is heated to reflux until the metallic Mg is spent, then returned to room temperature. 15 ml of THF and 0.73 g (3.4 mmol) of D-phenylalanine methyl ester hydrochloride are added. The mixture is stirred at room temperature for 16 hours; 15 ml of ethyl ether and 20 ml of a saturated aqueous $NH_4Cl$ solution are added. The organic phase is separated and the aqueous phase is washed with ethyl ether (3×10 ml). The organic phases are pooled and dried over $Na_2SO_4$. The mixture is filtered and evaporated under reduced pressure (25° C./24 mbar). The crude product is purified by means of chromatography through a silica gel column (eluent=from hexane:ethyl acetate 4:1 (v:v) to hexane:ethyl acetate 1:9 (v:v)). 1.1 g (1.7 mmol) of product are obtained whose $^1H$ NMR and mass spectra are consistent with the expected structure.

$[\alpha]_D = +47.2°$ (c=1.04, $CH_2Cl_2$).

EXAMPLE 36

Synthesis of the Ligand of Formula III, with $R_7$=methyl, $R_8$=methyl, $R_{11}$=tert-butyl, $R_{12}$=allyl 2,6-di-{[2,2-di-(2-allyloxy-5-tert-butyl-phenyl)-2-hydroxy-(R)-1-methyl-ethylimino]-methyl}-4-methyl-phenol 0.46 g (1 mmol) of (R)-(−)-2-amino-1,1-di-(2'-allyloxy-5'-tert-butyl-phenyl)-1-propanol and 0.083 g (0.5 mmol) of 2-hydroxy-5-methyl-1,3-benzenedicarboxaldehyde are dissolved in 15 ml of methanol. The mixture is stirred at room temperature for 4 hours and the solvent evaporated under reduced pressure (30° C./24 mbar). 0.51 g (0.5 mmol) of product are obtained, whose $^1$H NMR and mass spectra are consistent with the expected structure.

$[\alpha]_D = -337.7°$ (c=0.35, CH$_2$Cl$_2$)

EXAMPLE 37

Synthesis of the Ligand of Formula (C), with $R_7$=methyl, $R_5$=methyl, $R_{11}$=tert-butyl, $R_{12}$=6-hepten-1-yl 2,6-di-{[2,2-di-(5-tert-butyl-2-hept-6-enyloxy-phenyl)-2-hydroxy-(R)-1-methyl-ethylimino]-methyl}-4-methyl-phenol In the manner described in example 36, 0.138 g (0.84 mmol) of 2-hydroxy-5-methyl-1,3-benzenedicarboxaldehyde and 0.95 g (1.69 mmol) of (R)-(−)-2-amino-1,1-di-(5'-tert-butyl-2'-hept-6-enyloxy-phenyl)-1-propanol are reacted to obtain 1.05 g (0.84 mmol) of product, whose $^1$H NMR and mass spectra are consistent with the expected structure.

$[\alpha]_D = -122.7°$ (c=0.84, CH$_2$Cl$_2$).

EXAMPLE 38

Synthesis of the Ligand of Formula (C), with $R_7$=methyl, $R_8$=methyl, $R_{11}$=tert-butyl, $R_{12}$=10-undecen-1-yl 2,6-di-{[2,2-di-(5-tert-butyl-2-undec-10-enyloxy-phenyl)-2-hydroxy-(R)-1-methyl-ethylimino]-methyl}-4-methyl-phenol In the manner described in example 36, 0.1 g (0.61 mmol) of 2-hydroxy-5-methyl-1,3-benzenedicarboxaldehyde and 0.824 g (1.22 mmol) of (R)-(−)-2-amino-1,1-di-(5'-tert-butyl-2'-und-10-ecenyloxy-phenyl)-1-propanol are reacted to obtain 0.9 g (0.61 mmol) of product, whose $^1$H NMR and mass spectra are consistent with the expected structure.

$[\alpha]_D = -87.0°$ (c=1.06, CH$_2$Cl$_2$)

EXAMPLE 39

Synthesis of the Ligand of Formula (C), with $R_7$=methyl, $R_8$=methyl, $R_{11}$=tert-butyl, $R_{12}$=benzylvinyl 2,6-di-{[2,2-di-(5-tert-butyl-2-(4-vinyl-benzyloxy)-phenyl)-2-hydroxy-(R)-1-methyl-ethylimino]-methyl}-4-methyl-phenol In the manner described in example 36, 0.067 g (0.4 mmol) of 2-hydroxy-5-methyl-1,3-benzenedicarboxaldehyde and 0.48 g (0.8 mmol) of (R)-(−)-2-amino-1,1-di-[5'-tert-butyl-2'(4-vinyl-benzyloxy)-phenyl)]-1-propanol are reacted to obtain 0.53 g (0.4 mmol) of product, whose $^1$H NMR and mass spectra are consistent with the expected structure.

$[\alpha]_D = -123.0°$ (c=1.00, CH$_2$Cl$_2$)

EXAMPLE 40

Synthesis of the Ligand of Formula (C), with $R_7$=OR$_{10}$, $R_{10}$=4-vinylbenzyl, $R_8$=methyl, $R_{11}$=tert-butyl, $R_{12}$=octyl 2,6-di-{[2,2-di-(5-tert-butyl-2-octyloxy-phenyl)-2-hydroxy-(R)-1-methyl-ethylimino]-methyl)}-4-(4-vinyl-benzyloxy)-phenol In the manner described in example 36, 0.11 g (0.39 mmol) of 2-hydroxy-5-[(4-vinylbenzyl)oxy]isophthalaldehyde and 0.464 g (0.78 mmol) of (R)-(−)-2-amino-1,1-di-[5'-tert-butyl-2'-octyloxy-phenyl)-1-propanol are reacted to obtain 0.56 g (0.39 mmol) of product, whose $^1$H NMR and mass spectra are consistent with the expected structure.

$[\alpha]_D = -66.1°$ (c=1.05, CH$_2$Cl$_2$).

EXAMPLE 41

Synthesis of the Ligand of Formula (C), with $R_7$=vinylphenyl, $R_8$=methyl, $R_{11}$=tert-butyl, $R_{12}$=octyl 3,5-di-{[2,2-di-(5-tert-butyl-2-octyloxy-phenyl)-2-hydroxy-(R)-1-methyl-ethylimino]-methyl}-4-(4-vinyl-biphenyl-4-ol In the manner described in example 36, 0.1 g (0.4 mmol) of 4-hydroxy-4'-vinyl[1,1'-biphenyl]-3,5-dicarbaldehyde and 0.477 g (0.8 mmol) of (R)-(−)-2-amino-1,1-di-[5'-tert-butyl-2'-octyloxy-phenyl)-1-propanol are reacted to obtain 0.56 g (0.4 mmol) of product, whose $^1$H NMR and mass spectra are consistent with the expected structure.

$[\alpha]_D = -55.4°$ (c=0.64, CH$_2$Cl$_2$).

EXAMPLE 42

Synthesis of the Ligand of Formula (C), with $R_7$=OR$_{10}$, $R_{10}$=allyl, $R_8$=methyl, $R_{11}$=tert-butyl, $R_{12}$=octyl 4-Allyloxy-2,6-di-{[2,2-di-(5-tert-butyl-2-octyloxy-phenyl)-2-hydroxy-(R)-1-methyl-ethylimino]-methyl}phenol In the manner described in example 36, 0.062 g (0.3 mmol) of 5-(allyloxy)-2-hydroxy isophthalaldehyde and 0.355 g (0.6 mmol) of (R)-(−)-2-amino-1,1-di-[5'-tert-butyl-2'-octyloxy-phenyl)-1-propanol are reacted to obtain 0.4 g (0.3 mmol) of product, whose $^1$H NMR and mass spectra are consistent with the expected structure.

$[\alpha]_D = -92.3°$ (c=1.9, CH$_2$Cl$_2$).

EXAMPLE 43

Synthesis of the Ligand of Formula (C), with $R_7$=OR$_{10}$, $R_{10}$=undecenyl, $R_8$=methyl, $R_{11}$=tert-butyl, $R_{12}$=octyl 2,6-di-{[2,2-di-(5-tert-butyl-2-octyloxy-phenyl)-2-hydroxy-(R)-1-methyl-ethylimino]-methyl}-4-undec-10-enyloxy-phenol In the manner described in example 36, 0.04 g (0.125 mmol) of 2-hydroxy-5-(10-undecenyloxy)isophthalaldehyde and 0.15 g (0.25 mmol) of (R)-(−)-2-amino-1,1-di-[5'-tertbutyl-2'-octyloxy-phenyl)-1-propanol are reacted to obtain 0.18 g (0.125 mmol) of product, whose $^1$H NMR and mass spectra are consistent with the expected structure.

$[\alpha]_D = -35.7°$ (c=0.98, $CH_2Cl_2$).

EXAMPLE 44

Heterogenization of the Compound of Example 39 on a Polystyrene Matrix 0.2 mmol (0.27 g) of the compound of example 39, 0.65 ml of styrene (5.6 mmol) and 0.6 ml of 80% technical divinylbenzene (meta:para=2:1) are dissolved in 7 ml of toluene. 0.03 g of AIBN are added and the mixture is heated under reflux for 20 hours under vigorous stirring. 15 ml of methanol are added and a precipitate is obtained which is filtered off. The solid obtained is washed with dichloromethane (100 ml) and methanol (100 ml) then ground to obtain a powder. From the elemental analysis the degree of loading of the supported ligand is obtained, being equal to 0.2 mmol/g (N=0.56%).

The product thus obtained is suspended in methanol, then copper acetate monohydrate (0.4 mmol) is added in the presence of triethylamine (0.99 mmol, 0.1 ml). The product thus complexed with Cu(II) is maintained under reflux in acetonitrile for 16 hours in a Soxhlet extractor. The product thus obtained is dried under reduced pressure (25° C./0.013 mbar) for 3 hours.

The copper loading is determined by EA-ICP-MS analysis.

EXAMPLE 45

Heterogenization of the Compound of Example 40 on a Polystyrene Matrix 0.39 mmol (0.56 g) of the compound of example 40, 1.2 ml of styrene (11 mmol) and 1.2 ml of 80% technical divinylbenzene (meta:para=2:1) are dissolved in 7 ml of toluene. 0.04 g of AIBN are added and the mixture is heated under reflux for 20 hours under vigorous stirring. 15 ml of methanol are added and a precipitate is obtained which is filtered off. The solid obtained is washed with dichloromethane (100 ml) and methanol (100 ml) then ground to obtain a powder (1.9 g).

From the elemental analysis the degree of loading of the supported ligand is obtained, being equal to 0.125 mmol/g (N=0.35%).

The product thus obtained is suspended in methanol, then copper acetate monohydrate (0.25 mmol) is added in the presence of triethylamine (0.99 mmol, 0.1 ml). The product thus complexed with Cu(II) is maintained under reflux in acetonitrile for 16 hours in a Soxhlet extractor. The product thus obtained is dried under reduced pressure (25° C./0.013 mbar) for 3 hours.

The copper loading is determined by AEH-ICP-MS analysis.

EXAMPLE 46

Heterogenization of the Compound of Example 41 on a Polystyrene Matrix 0.3 mmol (0.42 g) of the compound of example 41, 1.1 ml of styrene (10 mmol) and 1.1 ml of 80% technical divinylbenzene (meta:para=2:1) are dissolved in 7 ml of toluene. 0.03 g of AIBN are added and the mixture is heated under reflux for 20 hours under vigorous stirring. 15 ml of methanol are added and a precipitate is obtained which is filtered off. The solid obtained is washed with dichloromethane (100 ml) and methanol (100 ml) then ground to obtain a powder (1.7 g). From the elemental analysis the degree of loading of the supported ligand is obtained, being equal to 0.06 mmol/g (N=0.17%).

The product thus obtained is suspended in methanol, then copper acetate monohydrate (0.12 mmol) is added in the presence of triethylamine (0.3 mmol, 0.03 ml). The product thus complexed with Cu(II) is maintained under reflux in acetonitrile for 16 hours in a Soxhlet extractor. The product thus obtained is dried under reduced pressure (25° C./0.013 mbar) for 3 hours.

The copper loading is determined by EA-ICP-MS analysis.

EXAMPLE 47

Heterogenization of the Ligand Described in Example 36 on a Hydropolysiloxane Matrix 0.975 g of methylhydrosiloxane-dimethylsiloxane copolymer (HMS-301 ABCR, Germany), 1.078 g of polydimethylsiloxane vinyldimethylsiloxane (DMS-V05 ABCR, Germany) and 0.16 g (0.156 mmol) of the ligand described in example 36 are dissolved in 1.5 ml of toluene. 0.01 g of the divinyltetramethyldisiloxane-Pt complex (3-3.5%) (ABCR, Germany) are added and the mixture is maintained under magnetic stirring and nitrogen flow for 20 hours. The crude product is ground, washed with dichloromethane (250 ml) and methanol (250 ml) and dried under reduced pressure (20° C./0.014 mbar).

From the elemental analysis the degree of loading of the supported ligand is obtained, being equal to 0.05 mmol/g (N=0.14%).

Following the method described in example 44 the supported complex is obtained. The copper loading is determined by EA-ICP-MS analysis.

EXAMPLE 48

Heterogenization of the Ligand Described in Example 37 on a Hydropolysiloxane Matrix 0.45 g of methylhydrosiloxane-dimethylsiloxane copolymer (HMS-301 ABCR, Germany), 0.27 g of polydimethylsiloxane vinyldimethylsiloxane (DMS-V05 ABCR, Germany) and 0.35 g (0.28 mmol) of the ligand described in example 37 are dissolved in 1.5 ml of toluene. 0.01 g of the divinyltetramethyldisiloxane-Pt complex (3-3.5%) (ABCR, Germany) are added and the mixture is maintained under magnetic stirring and nitrogen flow for 20 hours. The crude product is ground, washed with dichloromethane (250 ml) and methanol (250 ml) and dried under reduced pressure (20° C./0.014 mbar).

From the elemental analysis the degree of loading of the supported ligand is obtained, being equal to 0.05 mmol/g (N=0.5%).

Following the method described in example 44 the supported complex is obtained. The copper loading is determined by EA-ICP-MS analysis.

EXAMPLE 49

Heterogenization of the Ligand Described in Example 38 on a Hydropolysiloxane Matrix 0.32 g of methylhydrosiloxane-dimethylsiloxane copolymer (HMS-301 ABCR, Germany), 0.2 g of polydimethylsiloxane vinyldimethylsiloxane (DMS-V05 ABCR, Germany)

and 0.3 g (0.2 mmol) of the ligand described in example 38 are dissolved in 1.5 ml of toluene. 0.01 g of the divinyltetramethyldisiloxane-Pt complex (3-3.5%) (ABCR, Germany) are added and the mixture is maintained under magnetic stirring and nitrogen flow for 20 hours. The crude product is ground, washed with dichloromethane (250 ml) and methanol (250 ml) and dried under reduced pressure (20° C./0.014 mbar).

From the elemental analysis the degree of loading of the supported ligand is obtained, being equal to 0.09 mmol/g (N=0.25%).

Following the method described in example 44 the supported complex is obtained. The copper loading is determined by EA-ICP-MS analysis.

EXAMPLE 50

Heterogenization of the Ligand Described in Example 42 on a Hydropolysiloxane Matrix 0.33 g of methylhydrosiloxane-dimethylsiloxane copolymer (HMS-301 ABCR, Germany), 0.385 g of polydimethylsiloxane vinyldimethylsiloxane (DMS-V05 ABCR, Germany) and 0.4 g (0.3 mmol) of the ligand described in example 42 are dissolved in 1.5 ml of toluene. 0.01 g of the divinyltetramethyldisiloxane-Pt complex (3-3.5%) (ABCR, Germany) are added and the mixture is maintained under magnetic stirring and nitrogen flow for 20 hours. The crude product is ground, washed with dichloromethane (250 ml) and methanol (250 ml) and dried under reduced pressure (20° C./0.014 mbar).

From the elemental analysis the degree of loading of the supported ligand is obtained, being equal to 0.075 mmol/g (N=0.21%).

Following the method described in example 44 the supported complex is obtained. The copper loading is determined by EA-ICP-MS analysis.

EXAMPLE 51

Heterogenization of the Ligand Described in Example 43 on a Hydropolysiloxane Matrix 0.1 g of methylhydrosiloxane-dimethylsiloxane copolymer (HMS-301 ABCR, Germany), 0.11 g of polydimethylsiloxane vinyldimethylsiloxane (DMS-V05 ABCR, Germany) and 0.18 g (0.12 mmol) of the ligand described in example 43 are dissolved in 1.5 ml of toluene. 0.01 g of the divinyltetramethyldisiloxane-Pt complex (3-3.5%) (ABCR, Germany) are added and the mixture is maintained under magnetic stirring and nitrogen flow for 20 hours. The crude product is ground, washed with dichloromethane (250 ml) and methanol (250 ml) and dried under reduced pressure (20° C./0.014 mbar).

From the elemental analysis the degree of loading of the supported ligand is obtained, being equal to 0.065 mmol/g (N=0.18%).

Following the method described in example 44 the supported complex is obtained. The copper loading is determined by EA-ICP-MS analysis.

EXAMPLE 52

Synthesis of Chrysanthemic Acid Promoted by the Heterogeneous Catalyst Described in Example 44

0.2 g of the catalyst whose preparation is described in example 44 are suspended in 3 ml of acetonitrile then 0.096 mmol (0.01 g) of phenylhydrazine in 3 ml of acetonitrile are added. The reaction mixture is heated to 50° C. and 0.1 ml of a solution containing 0.21 ml (2 mmol) of ethyl diazoacetate in 3 ml acetonitrile is added. 10 mmol of 2,5-dimethyl-2,4-hexadiene (1.4 ml) are then added, followed by the remaining 2.9 ml of the ethyl diazoacetate solution in acetonitrile, added over a period of about 1 hour. The reaction mixture is maintained under stirring at 50° C. for 6 hours. The catalyst is removed by filtration and washed with 20 ml of dichloromethane. 0.2 g of ethyl chrysanthemate are obtained.

Following basic hydrolysis, acidification and extraction with dichloromethane, chrysanthemic acid with the following composition is obtained:

cis/trans=43/57; $ee_{cis}$=50%; $ee_{trans}$=69%

EXAMPLE 53

Synthesis of Chrysanthemic Acid Promoted by the Recycled Heterogeneous Catalyst of Example 52

The catalyst recovered after the first reactive cycle of example 52 is reused in a second catalytic cycle following the same method as described in example 52. 0.145 g of ethyl chrysanthemate are obtained.

Following basic hydrolysis, acidification and extraction with dichloromethane, chrysanthemic acid with the following composition is obtained:

cis/trans=40/60; $ee_{cis}$=34%; $ee_{trans}$=35%

EXAMPLE 54

Synthesis of Chrysanthemic Acid Promoted by the Heterogeneous Catalyst Described in Example 45

In the manner described in example 52, using 0.64 g of the catalyst prepared as in example 45, 0.172 g of ethyl chrysanthemate are obtained.

Following basic hydrolysis, acidification and dichloromethane extraction, chrysanthemic acid with the following composition is obtained:

cis/trans=42/58; $ee_{cis}$=64%; $ee_{trans}$=75%

EXAMPLE 55

Synthesis of Chrysanthemic Acid Promoted by the Recycled Heterogeneous Catalyst of Example 54

The catalyst recovered after the first reactive cycle of example 54 is reused in two further catalytic cycles following the same method as described in example 52. 0.133 g and 0.137 g of ethyl chrysanthemate are obtained, respectively.

Following basic hydrolysis, acidification and extraction with dichloromethane, chrysanthemic acid with the following composition is obtained:

$2^{nd}$ cycle: cis/trans=41/59; $ee_{cis}$=48%; $ee_{trans}$=56%
$3^{rd}$ cycle: cis/trans=40/60; $ee_{cis}$=14%; $ee_{trans}$=33%

EXAMPLE 56

Synthesis of Chrysanthemic Acid Promoted by the Heterogeneous Catalyst Described in Example 46

In the manner described in example 52, using 0.66 g of the catalyst prepared as in example 46, 0.165 g of ethyl chrysanthemate are obtained.

Following basic hydrolysis, acidification and dichloromethane extraction, chrysanthemic acid with the following composition is obtained:
cis/trans=42/58; $ee_{cis}$=59%; $ee_{trans}$=74%

EXAMPLE 57

Synthesis of Chrysanthemic Acid Promoted by the Recycled Heterogeneous Catalyst of Example 56

The catalyst recovered after the first reactive cycle of example 56 is reused in a second catalytic cycle following the same method as described in example 52. 0.128 g of ethyl chrysanthemate are obtained.
Following basic hydrolysis, acidification and extraction with dichloromethane, chrysanthemic acid with the following composition is obtained:
$2^{nd}$ cycle: cis/trans=42/58; $ee_{cis}$=54%; $ee_{trans}$=66%

EXAMPLE 58

Synthesis of Chrysanthemic Acid Promoted by the Heterogeneous Catalyst Described in Example 47

In the manner described in example 52, using 0.8 g of the catalyst prepared as in example 47, 0.075 g of ethyl chrysanthemate are obtained.
Following basic hydrolysis, acidification and extraction with dichloromethane, chrysanthemic acid with the following composition is obtained:
cis/trans=38/62; $ee_{cis}$=25%; $ee_{trans}$=26%

EXAMPLE 59

Synthesis of Chrysanthemic Acid Promoted by the Heterogeneous Catalyst Described in Example 48

In the manner described in example 52, using 0.23 g of the catalyst prepared as in example 48, 0.137 g of ethyl chrysanthemate are obtained.
Following basic hydrolysis, acidification and dichloromethane extraction, chrysanthemic acid with the following composition is obtained:
cis/trans=40/60; $ee_{cis}$=38%; $ee_{trans}$=46%

EXAMPLE 60

Synthesis of Chrysanthemic Acid Promoted by the Heterogeneous Catalyst Described in Example 49

In the manner described in example 52, using 0.45 g of the catalyst prepared as in example 49, 0.157 g of ethyl chrysanthemate are obtained.
Following basic hydrolysis, acidification and dichloromethane extraction, chrysanthemic acid with the following composition is obtained:
cis/trans=41/59; $ee_{cis}$=59%; $ee_{trans}$=63%

EXAMPLE 61

Synthesis of Chrysanthemic Acid Promoted by the Recycled Heterogeneous Catalyst of Example 60

The catalyst recovered after the first reactive cycle of example 60 is reused in three further catalytic cycles following the same method as described in example 52. 0.208 g, 0.188 and 0.176 g of ethyl chrysanthemate are obtained.

Following basic hydrolysis, acidification and extraction with dichloromethane, chrysanthemic acid with the following composition is obtained:
$2^{nd}$ cycle: cis/trans=40/60; $ee_{cis}$=58%; $ee_{trans}$=61%
$3^{rd}$ cycle: cis/trans=38/62; $ee_{cis}$=43%; $ee_{trans}$=44%
$4^{th}$ cycle: cis/trans=39/61; $ee_{cis}$=21%; $ee_{trans}$=24%

EXAMPLE 62

Synthesis of Chrysanthemic Acid Promoted by the Heterogeneous Catalyst Described in Example 50

In the manner described in example 52, using 0.53 g of the catalyst prepared as in example 50, 0.176 g of ethyl chrysanthemate are obtained.
Following basic hydrolysis, acidification and extraction with dichloromethane, chrysanthemic acid with the following composition is obtained:
cis/trans=41/59; $ee_{cis}$=32%; $ee_{trans}$=53%

EXAMPLE 63

Synthesis of Chrysanthemic Acid Promoted by the Recycled Heterogeneous Catalyst of Example 62

The catalyst recovered after the first reactive cycle of example 62 is reused in two further catalytic cycles following the same method as described in example 52. 0.117 g and 0.078 g of ethyl chrysanthemate are obtained, respectively.
Following basic hydrolysis, acidification and extraction with dichloromethane, chrysanthemic acid with the following composition is obtained:
$2^{nd}$ cycle: cis/trans=40/60; $ee_{cis}$=26%; $ee_{trans}$=49%
$3^{rd}$ cycle: cis/trans=40/60; $ee_{cis}$=12%; $ee_{trans}$=25%

EXAMPLE 64

Synthesis of Chrysanthemic Acid Promoted by the Heterogeneous Catalyst Described in Example 51

In the manner described in example 52, using 0.61 g of the catalyst prepared as in example 51, 0.117 g of ethyl chrysanthemate are obtained.
Following basic hydrolysis, acidification and extraction with dichloromethane, chrysanthemic acid with the following composition is obtained:
cis/trans=41/59; $ee_{cis}$=56%; $ee_{trans}$=70%

EXAMPLE 65

Synthesis of Chrysanthemic Acid Promoted by the Recycled Heterogeneous Catalyst of Example 64

The catalyst recovered after the first reactive cycle of example 64 is reused in a second catalytic cycle following the same method as described in example 52. 0.149 g of ethyl chrysanthemate are obtained.
Following basic hydrolysis, acidification and extraction with dichloromethane, chrysanthemic acid with the following composition is obtained:
$2^{nd}$ cycle: cis/trans=40/60; $ee_{cis}$=20%; $ee_{trans}$=38%

The invention claimed is:
1. A method for preparing enantiomerically enriched d-(+) trans chrysanthemic acid, comprising:
a. reacting a diazoacetate of the formula (H) with 2,5-dimethyl-2,4-hexadiene

$$N_2=CH-COOR_1 \qquad (H)$$

where $R_1$ is a linear or branched $C_1$-$C_8$ alkyl, possibly substituted with one or two $C_5$-$C_{10}$ alicyclic groups, $C_6$-$C_{10}$ aryl unsubstituted or substituted with 1, 2, 3, $C_1$-$C_4$ alkyl groups, $C_7$-$C_{11}$ aralkyl unsubstituted or substituted on the ring with 1, 2, 3 $C_1$-$C_4$ alkyl groups, a $C_5$-$C_{10}$ alicyclic group unsubstituted or substituted by 1, 2, 3 $C_1$-$C_4$ alkyl groups or cyclohexyl;

characterised in that in step a), a supported complex of formula (A) is used

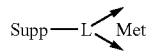
(A)

in which Supp is an organic or inorganic type matrix, wherein when Supp is an inorganic type matrix, it comprises a silica matrix and when Supp is an organic type matrix, it comprises a polymer matrix selected from the group consisting of styrene polymers, styrene/divinylbenzene copolymers and hydropolysiloxanes, Met is Cu (II) or (I), L is a ligand containing at least one asymmetric carbon atom and at least one spacer chain which forms covalent bonds with said organic or inorganic type matrix, said ligand being coordinated by complexation to the aforesaid transition metal ions; said ligand L being derived from a ligand $L_a$ selected from the group consisting of:

(1) optically active bisoxazolines of the general formula (B):

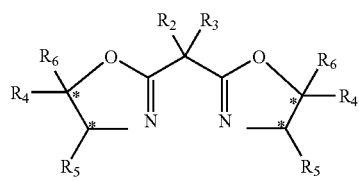
(B)

and (2) optically active salicylaldimines of the general formula (C):

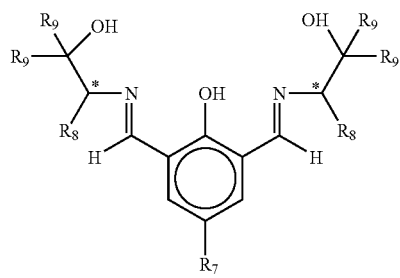
(C)

where:

*indicates a stereogenic centre, $R_2$ and $R_3$, the same or different, are chosen from: hydrogen, methyl, $C_3$-$C_{11}$ alkenyl, 4-vinylbenzyl the group of formula

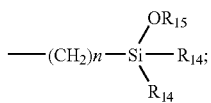
(E)

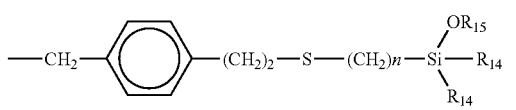
(F)

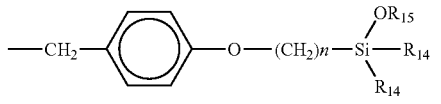
(G)

where n is an integer between 3 and 11, $R_{14}$ is $C_1$-$C_2$ alkyl or a —$OR_{15}$ group where $R_{15}$ is $C_1$-$C_2$ alkyl, and those obtained from the reaction of the compound of formula (B) having $R_2$=$R_3$=alkenyl $C_3$ or $R_2$=$R_3$=alkenyl $C_{11}$ with 3 mercaptopropyl-trimethoxysilane, with the proviso that at least one of the $R_2$ and $R_3$ groups has a functionality able to polymerise or able to bind to an organic or inorganic polymer; $R_4$ is H, $R_5$ and $R_6$ are the same and are selected from phenyl, naphthyl, benzyl, or $R_5$ and $R_6$ are bound together to form 1,2-indandiyl, $R_7$ is chosen from hydrogen, methyl, tert-butyl, phenyl, vinyl phenyl, a —$OR_{10}$ group where $R_{10}$ is, $C_3$-$C_{11}$ alkenyl, vinylphenyl, 4-vinylbenzyl; $R_8$ is chosen from methyl, benzyl; $R_9$ is a group of formula (D)

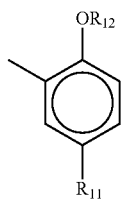
(D)

where $R_{11}$ is tert-butyl, tert-octyl; $R_{12}$ is n-butyl, n-octyl, $C_3$-$C_{11}$, alkenyl, benzyl, 4-vinylbenzyl, with the proviso that at least one of the $R_7$ and $R_9$ groups has alkenyl functionality able to polymerize or able to bind to an already formed organic or inorganic polymer matrix.

b. reacting the chrysanthemic acid esters with an acid or base to form said enantiomerically enriched form of chrystanthemic acid.

2. The method according to claim 1, wherein Met is Cu(II) or (I).

3. The method according to claim 1, wherein n of formulas, (E), (F), (G), (H) is 3.

4. The method according to claim 1, wherein when $L_a$ belongs to class (1), it is selected from the compounds of formula (B) in which:

$R_2$=$R_3$=4-vinylbenzyl, $R_4$=H, $R_5$ bound to $R_6$=1,2-indandiyl, $R_2$=$R_3$=4-vinylbenzyl, $R_4$=H, $R_5$=$R_6$=phenyl, $R_2$=$R_3$=allyl, $R_4$=H, $R_5$ bound to $R_6$=1,2-indandiyl $R_2$=$R_3$=allyl, $R_4$=H, $R_5$=$R_6$=phenyl, $R_2$=$R_3$=6-hepten-1-yl $R_4$=H, $R_5$=$R_6$=phenyl, $R_2$=$R_3$=10-undecen-1-yl, $R_4$=H, $R_5$=$R_6$=phenyl $R_2=R_3=$are the substituents coming from reacting (B) in which $R_2=R_3=$4-vinylbenzyl with 3-mercapto-propyl-trimethoxysilane, $R_4=$H, $R_5=R_6=$phenyl;

$R_2=R_3=$are the substituents coming from reacting (B) in which $R_2=R_3=$allyl with 3-mercapto-propyl-trimethoxysilane, $R_4=$H, $R_5=R_6=$phenyl;

$R_2=R_3=$are the substituents coming from reacting (B) in which $R_2=R_3=$undecen-1-yl with 3-mercapto-propyl-trimethoxysilane, $R_4=$H, $R_5=R_6=$phenyl;

$R_2=R_3=$are the substituents coming from reacting the compound of formula (B) having $R_2=R_3=$4-vinylbenzyl, $R_4=$H, $R_5$ bound to $R6=$1,2-indandiyl.

5. The method according to claim 1, wherein $L_a$ belongs to class (2), the same is chosen from one of the compounds of formula (C) in which:

$R_7=R_8=$methyl, $R_9$ is a group of formula (D) in which $R_{11}=$tert-butyl, $R_{12}=$allyl, $R_7=R_8=$methyl, $R_9$ is a group of formula (D) in which $R_{11}=$tert-butyl, $R_{12}=$6-hepten-1-yl, $R_7=R_8=$methyl, $R_9$ is a group of formula (D) in which $R_{11}=$tert-butyl, $R_{12}=$10-undecen-1-yl $R_7=R_8=$methyl, $R_9$ is a group of formula (D) in which $R_{11}=$tert-butyl, $R_{12}=$benzylvinyl, $R_7=$—$OR_{10}$, $R_{10}=$4-vinylbenzyl, $R_8=$methyl, $R_9$ is a group of formula (D) in which $R_{11}=$tert-butyl, $R_{12}=$octyl $R_7=$vinylphenyl, $R_8=$methyl, $R_9$ is a group of formula (D) in which $R_{11}=$tert-butyl, $R_{12}=$octyl, $R_7=$—$OR_{10}$, $R_{10}=$allyl, $R_8=$methyl, $R_9$ is a group of formula (D) in which $R_{11}=$tert-butyl, $R_{12}=$octyl, $R_7=$—$OR_{10}$, $R_{10}=$10-undecen-1-yl, $R_8=$methyl, $R_9$ is a group of formula (D) in which $R_{11}=$tert-butyl, $R_{12}=$octyl.

6. The method according to claim 1, wherein in the diazoacetate of formula (H), $R_1$ is linear or branched $C_1$-$C_4$ alkyl, phenyl, benzyl, dimethylbenzyl, cyclohexyl, cycloheptyl, cyclooctyl, dicyclohexylmethyl, (d,l)-menthyl.

* * * * *